(12) United States Patent
Hutchinson et al.

(10) Patent No.: US 11,403,754 B2
(45) Date of Patent: Aug. 2, 2022

(54) METHOD AND APPARATUS FOR MONITORING OF A HUMAN OR ANIMAL SUBJECT

(71) Applicant: OXEHEALTH LIMITED, Oxford (GB)

(72) Inventors: Nicholas Dunkley Hutchinson, Oxford (GB); Simon Mark Chave Jones, Oxford (GB)

(73) Assignee: OXEHEALTH LIMITED, London (GB)

( * ) Notice: Subject to any disclaimer, the term of this patent is extended or adjusted under 35 U.S.C. 154(b) by 274 days.

(21) Appl. No.: 16/732,769

(22) Filed: Jan. 2, 2020

(65) Prior Publication Data

US 2020/0250816 A1 Aug. 6, 2020

(30) Foreign Application Priority Data

Jan. 2, 2019 (GB) .................................... 1900032

(51) Int. Cl.
*G06T 7/00* (2017.01)
*G06T 7/70* (2017.01)
(Continued)

(52) U.S. Cl.
CPC .......... *G06T 7/0012* (2013.01); *A61B 5/0077* (2013.01); *A61B 5/02416* (2013.01);
(Continued)

(58) Field of Classification Search
CPC ... A61B 5/0077; A61B 5/746; A61B 5/02416; A61B 5/1128; A61B 5/7221;
(Continued)

(56) References Cited

U.S. PATENT DOCUMENTS 8,855,384 B2 10/2014 Kyal et al.
8,965,090 B1 2/2015 Khachaturian et al.
(Continued)

FOREIGN PATENT DOCUMENTS

EP 0615245 A2 9/1994
EP 0919184 A1 6/1999
(Continued)

OTHER PUBLICATIONS

European Search Report regarding Application No. 19220090.5-115 dated Feb. 24, 2020.
(Continued)

*Primary Examiner* — Brenda C Bernardi
(74) *Attorney, Agent, or Firm* — Harness, Dickey & Pierce, P.L.C.

(57) ABSTRACT

A method and apparatus for monitoring a human or animal subject in a room using video imaging of the subject and analysis of the video image to detect and quantify movement of the subject and to derive an estimate of vital signs such as heart rate or breathing rate. The method includes techniques for de-correlating global intensity variations such as sunlight changes, compensating for noise, eliminating areas not of interest in the image, and quickly and automatically finding regions of interest for detecting subject movement and estimating vital signs. A logic machine is used for interpreting detected movement of the subject, and an artificial neural network is used to calculate a confidence measure for the vital signs estimates from signal quality indices. The confidence measure may be used with a normal density filter to output estimates of the vital signs.

20 Claims, 11 Drawing Sheets

(51) Int. Cl.
*A61B 5/00* (2006.01)
*A61B 5/024* (2006.01)
*A61B 5/08* (2006.01)
*A61B 5/11* (2006.01)
*G06T 7/20* (2017.01)

(52) U.S. Cl.
CPC .......... *A61B 5/0816* (2013.01); *A61B 5/1128* (2013.01); *A61B 5/746* (2013.01); *G06T 7/20* (2013.01); *G06T 7/70* (2017.01); *A61B 2503/40* (2013.01); *G06T 2207/10016* (2013.01); *G06T 2207/20081* (2013.01); *G06T 2207/30048* (2013.01)

(58) Field of Classification Search
CPC ... A61B 5/0816; A61B 5/113; A61B 2503/40; G06T 7/0012; G06T 7/70; G06T 7/0016; G06T 7/20; G06T 2207/20081; G06T 2207/10016; G06T 2207/30048; G06T 2207/30076
See application file for complete search history.

(56) References Cited

U.S. PATENT DOCUMENTS

| | | |
|---|---|---|
| 9,036,877 B2 | 5/2015 | Kyal et al. |
| 10,034,979 B2 | 7/2018 | Bechtel et al. |
| 10,292,662 B2 | 5/2019 | Kirenko |
| 2002/0106709 A1 | 8/2002 | Potts et al. |
| 2002/0180870 A1 | 12/2002 | Chen |
| 2003/0138149 A1 | 7/2003 | Iizuka et al. |
| 2003/0228032 A1 | 12/2003 | Rui et al. |
| 2005/0197590 A1 | 9/2005 | Osorio et al. |
| 2006/0058618 A1 | 3/2006 | Nishiura |
| 2007/0156060 A1 | 7/2007 | Cervantes |
| 2007/0195931 A1 | 8/2007 | Ohisi |
| 2008/0292151 A1 | 11/2008 | Kurtz et al. |
| 2009/0216499 A1 | 8/2009 | Tobola et al. |
| 2010/0049064 A1 | 2/2010 | Bodmer et al. |
| 2010/0074475 A1 | 3/2010 | Chouno |
| 2010/0298656 A1 | 11/2010 | McCombie et al. |
| 2011/0046498 A1 | 2/2011 | Klap et al. |
| 2011/0150274 A1 | 6/2011 | Patwardhan et al. |
| 2011/0251493 A1 | 10/2011 | Poh et al. |
| 2011/0311143 A1 | 12/2011 | Cennini et al. |
| 2012/0141000 A1 | 6/2012 | Jeanne et al. |
| 2012/0213405 A1 | 8/2012 | Sasaki |
| 2012/0242819 A1 | 9/2012 | Schamp |
| 2013/0138009 A1 | 5/2013 | Nierenberg et al. |
| 2013/0324875 A1 | 12/2013 | Mestha et al. |
| 2014/0003690 A1 | 1/2014 | Razeto et al. |
| 2014/0023235 A1 | 1/2014 | Cennini et al. |
| 2014/0037163 A1 | 2/2014 | Kirenko et al. |
| 2014/0037166 A1 | 2/2014 | De Haan et al. |
| 2014/0236036 A1 | 8/2014 | de Haan et al. |
| 2014/0276099 A1 | 9/2014 | Kirenko et al. |
| 2014/0276104 A1 | 9/2014 | Tao et al. |
| 2014/0334697 A1 | 11/2014 | Kersten et al. |
| 2014/0371599 A1 | 12/2014 | Wu et al. |
| 2014/0371635 A1 | 12/2014 | Shinar et al. |
| 2014/0378842 A1 | 12/2014 | Xu et al. |
| 2015/0005646 A1 | 1/2015 | Balakrishnan et al. |
| 2015/0063708 A1 | 3/2015 | Sripadarao et al. |
| 2015/0104088 A1 | 4/2015 | Kirenko et al. |
| 2015/0148687 A1 | 5/2015 | Kitajima et al. |
| 2015/0208987 A1 | 7/2015 | Shan et al. |
| 2015/0221069 A1 | 8/2015 | Shaburova et al. |
| 2015/0250391 A1 | 9/2015 | Kyal et al. |
| 2015/0363361 A1 | 12/2015 | Kniazev |
| 2016/0106340 A1 | 4/2016 | Mestha et al. |
| 2016/0125260 A1 | 5/2016 | Huang et al. |
| 2016/0132732 A1 | 5/2016 | Gunther et al. |
| 2016/0210747 A1 | 7/2016 | Hay et al. |
| 2016/0220128 A1* | 8/2016 | Den Brinker ........ A61B 5/0008 |
| 2016/0253820 A1 | 9/2016 | Jeanne et al. |
| 2016/0310067 A1 | 10/2016 | Heinrich et al. |
| 2017/0007185 A1 | 1/2017 | Lin et al. |
| 2017/0042432 A1 | 2/2017 | Adib et al. |
| 2017/0224256 A1 | 8/2017 | Kirenko |
| 2017/0238805 A1 | 8/2017 | Addison et al. |
| 2017/0238842 A1 | 8/2017 | Jacquel et al. |
| 2018/0085010 A1 | 3/2018 | Jopnes et al. |
| 2018/0279885 A1 | 10/2018 | Bulut |
| 2019/0000391 A1 | 1/2019 | De Haan et al. |
| 2019/0029543 A1* | 1/2019 | Hutchinson .......... A61B 5/7485 |
| 2019/0267040 A1 | 8/2019 | Ikeda et al. |

FOREIGN PATENT DOCUMENTS

| | | |
|---|---|---|
| EP | 1571594 A2 | 9/2005 |
| EP | 2767233 A1 | 8/2014 |
| EP | 2976998 A1 | 1/2016 |
| EP | 2988274 A2 | 2/2016 |
| EP | 3073905 A1 | 10/2016 |
| EP | 3207862 A1 | 8/2017 |
| JP | 2011130996 A | 7/2011 |
| KR | 100812996 B1 | 3/2008 |
| WO | WO-2010/100593 A1 | 9/2010 |
| WO | WO-2010/115939 A2 | 10/2010 |
| WO | WO-2011021128 A2 | 2/2011 |
| WO | WO-2013027027 A2 | 2/2013 |
| WO | WO-2014125250 A1 | 8/2014 |
| WO | WO-2014131850 A1 | 9/2014 |
| WO | WO-2014140994 A1 | 9/2014 |
| WO | WO-201504915 A1 | 1/2015 |
| WO | WO-2015049150 A1 | 4/2015 |
| WO | WO-2015055709 A1 | 4/2015 |
| WO | WO-2015/078735 A1 | 6/2015 |
| WO | WO-2015/091582 A1 | 6/2015 |
| WO | WO-2015172735 A1 | 11/2015 |
| WO | WO-2016092290 A1 | 6/2016 |
| WO | WO-2016094749 A1 | 6/2016 |
| WO | WO-2016159151 A1 | 10/2016 |
| WO | WO-2017125743 A1 | 7/2017 |
| WO | WO-2017125744 A1 | 7/2017 |
| WO | WO-2017125763 A1 | 7/2017 |

OTHER PUBLICATIONS

An Efficient Approach for Object Detection and Tracking of Objects in a Video with Variable Background, Kumar S. Ray and Soma Chakraborty, May 11, 2017.
Foreground detection, May 5, 2020, https://en.wikipedia.org/w/index.php?title=Foreground_detection&oldid=854014910.
Carbon-atom wires produced by nanosecond pulsed laser deposition in a baground gas, Casari, et al., Dept. of Energy, Via Ponzio 34/3 Milan, Italy (2016 190-195.
R. Janmohamed et al, Study of Porous Carbon Thin Films produced by Pulsed Laser Deposition, Dept. of Electrical and Computer Engineering, Univ. of Alberta, Edmonton, Canada, Applied Surface Science (2007) 7964-7968.
D. Vick, et al, Production of porous carbon thin films by pulsed laser deposition, Dept. of Electrical and Computer Engineering, Univ. of Alberta, Canada, Feb. 6, 1999.
Making porous conductive carbon films with unbalanced magnetron sputtering, Kim, et al, Japanese Journal of Applied Physics 54, (2015).
Andreas Stein et al, Functionalization of Porous Carbon Materials with Designed Pore Architecture, Advanced Materials, 2008, 20, 1-29.
Kononenko et al, Pulsed laser deposition of hard carbon coatings at atmospheric pressure, Quantum Electronics 33(3) 189-191 (2003).
Thareja, et al, Pulsed Laser Deposition of Carbon Films, Department of Physics and Centre for Laser Technology, Indian Institute of Tech., Kanpur 208 016 (UP) India.
Yap, et al, Nanostructured Diamond-Like Carbon Films Grown by Off-Axis Pulsed Laser Deposition, Hindawi Pub. Corp. vol. 2015, Article ID 731306, Sep. 4, 2015.

(56) References Cited

OTHER PUBLICATIONS

Melios, et al, Detection of Ultra-Low Concentration NO in Complex Environment Using Epitaxial Graphene Sensors, American Chemical Society.
Henley, et al, Dynamics of Confirmed Plumes During Short and Ultrashort Pulsed Laser Ablation of Graphite, Physical Review B 72, 205413, (2005).
Rode, et al, Formation of Cluster-Assembled Carbon Nano-Foam by High-Repetition Rate Laser Ablation, Applied Physics A Materials Science & Processing, 135-144 (2000).
Yavari, et al, High Sensitivity Gas Detection Using a Macroscopic Three-Dimensional Graphene Foam Network, Scientific Reports, Sep. 30, 2011.
Inagaki, et al, Carbon foam: preparation and application, Carbon (2015).
Eduard Llobet, Gas Sensors Using Carbon Nanomaterials: A Review, Sensors and Actuators B 179 (2013) 32-45.
Armentano, et al, Sensors for sub-ppm No Gas Detection based on Carbon Nanotube Thin Films, Applied Physics Letters, Feb. 2003.
Rode, et al, Structural Analysis of a Carbon Foam Formed by High Pulse-Rate Laser Ablation, Appl. Phys. A 69 (Suppl.) S755-S758 (1999).
Search Report of UKIPO regarding Application No. GB1900033.0 dated Jun. 13, 2019.
British Search Report regarding Appliction No. 1900034.8 dated Jun. 13, 2019.
Nathalie M. El Nabbout et al, "Automatically Detecting and Tracking People Walking through a Transparent Door with Vision", Computer and Robot Vision, 2008. CRV '08. Canadian Conference on, IEEE, Piscataway, NJ, USA, May 28, 2008 (May 28, 2008), pp. 171-178.
Qiang Zhu et al, "Learning a Sparse, Corner-Based Representation for Corner-Based Representation for Time-varying Background Modeling", Computer Vision, 2005. ICCV 2005. Tenth IEEE International Conference on Beijing, China Oct. 17-20, 2005, Piscataway, NJ, USA, IEEE, Los Alamitos, CA, USA, vol. 1, Oct. 17, 2005 (Oct. 17, 2005), pp. 678-685.
Konstantinos Avgerinakis et al, "Activity detection and recognition of daily living events", Proceedings of the 1st ACM International Workshop on Multimedia Indexing and Information Retrieval for Healthcare, MIIRH '13, Oct. 22, 2013 (Oct. 22, 2013), pp. 1-7.
Arindam Sikdar et al, "Computer-Vision-Guided Human Pulse Rate Estimation: A Review", IEEE Reviews in Biomedical Engineering, vol. 9, Sep. 16, 2016 (Sep. 16, 2016), pp. 91-105.
Yu Sun et al, "Photoplethysmography Revisited: From Contact to Noncontact, From Point to Imaging", IEEE Transactions on Biomedical Engineering, IEEE Service Center, Piscataway, NJ, USA, vol. 63, No. 3, Mar. 1, 2016 (Mar. 1, 2016), pp. 463-477.
Tongchi Zhou et al, "A study of relative motion point trajectories for action recognition", 2015 International Conference on Wireless Communications & Signal Processing (WCSP), IEEE, Oct. 15, 2015 (Oct. 15, 2015), pp. 1-5.
Hisato Aota et al, "Extracting objects by clustering of full pixel trajectories", Signal Processing and Multimedia Applications (SIGMAP), Proceedings of the 2010 International Conference On, IEEE, Jul. 26, 2010 (Jul.. 26, 2010), pp. 65-72.
Shandong Wu et al, "A hierarchical motion trajectory signature descriptor", 2008 IEEE International Conference on Robotics and Automation. The Half-Day Workshop on: Towards Autonomous Agriculture of Tomorrow, IEEE—Piscataway, NJ, USA, Piscataway, NJ, USA, May 19, 2008 (May 19, 2008), pp. 3070-3075.
Search Report for GB Application No. 1618828.6, dated Mar. 31, 2017.
International Search Report and Written Opinion for PCT/GB2017/053343, dated Jan. 4, 2018; ISA/EP.
International Search Report and Written Opinion for PCT/GB2017/052779, dated Nov. 10, 2017; ISA/EP.
Search Report for GB Application No. 1615899.0, dated Feb. 28, 2017.
International Preliminary Report on Patentability and Written Opinion regarding Applicaiton No. PCT/GB2017/052779 dated Mar. 19, 2019.
International Search Report for PCT/GB2017/050162, ISA/EP, Rijswijk, NL, dated Jul. 6, 2017.
Written Opinion of the ISA for PCT/GB2017/050162, ISA/EP, Rijswijk, NL, dated Jul. 6, 2017.
Search Report for Priority Application GB1601140.5, UK IPO, Newport, South Wales, dated Jul. 21, 2016.
International Search Report for PCT/GB2017/050127, ISA/EP, Rijswijk, NL, dated Mar. 28, 2017.
Written Opinion of the ISA for PCT/GB2017/050127, ISA/EP, Rijswijk, NL, dated Mar. 28, 2017.
UK IPO Search Report under Section 17(5) for priority application GB1061143.9, dated Mar. 30, 2016.
International Search Report for PCT/GB2017/050128, ISA/EP, Rijswijk, NL, dated Apr. 13, 2017.
Written Opinion of the ISA for PCT/GB2017/050128, ISA/EP, Rijswijk, NL, dated Apr. 13, 2017.
Search Report under Section 17(5) for priority application GB1601142.1, UKIPO, Newport, South Wales, dated Jun. 28, 2016.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
International Search Report for PCT/GB2017/050126, ISA/EP, Rijswijk, NL, dated Apr. 20, 2017.
Written Opinion of the ISA for PCT/GB2017/050126, ISA/EP, Rijswijk, NL, dated Apr. 20, 2017.
UK IPO Search Report for GB priority application 1601217.1, Newport, South Wales, dated Jul. 25, 2016.
Search Report regarding United Kingdom Patent Application No. GB1706449.4, dated Oct. 25, 2017.
Amelard Robert et al. "Illumination-compensated non-contact imaging photoplethysmography via dual-mode temporally coded illumination". Progress in Biomedical Optics and Imaging, SPIE—International Society for Optical Engineering, Bellingham, WA, US., vol. 9316, Mar. 5, 2015.
Blocker Timon et al, "An online PPGI approach for camera based heart rate monitoring using beat-to-beat detection", 2017 IEEE Sensors Applications Symposium (SAS), IEEE, Mar. 13, 2017.
Extended European Search Report regarding applicaiton No. 18168310.3-1115 dated Oct. 1, 2018.
European Search Report regarding Application No. EP 19 15 8085 dated Jul. 10, 2019.
Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).
Remote Plethysmorgraphic Imaging Using Ambient Light, Verkruysse, Dec. 22, 2008.
Real Time Automated Detection of Clonic Seizures in Newbors, Pisani, 2014.
Distance PPG: Robust Noncontact Vital Signs Monitoring Using a Camera, Kumar, 2015.
Extended EP Search Report regarding Application No. 19220090.5 dated Feb. 24, 2020.

\* cited by examiner

METHOD AND APPARATUS FOR MONITORING OF A HUMAN OR ANIMAL SUBJECT

CROSS-REFERENCE TO RELATED APPLICATIONS

This application discloses similar subject matter to the two co-pending US applications of the same date and in the same name which are hereby incorporated by reference, and is related to United Kingdom patent application numbers 1900032.2, 1900033.0 and 1900034.8 all filed 2 Jan. 2019 and the contents of which are also hereby incorporated by reference.

FIELD

The present invention relates to a method and apparatus for monitoring a human or animal subject, and in particular a subject within an enclosed area, e.g. a room such as a secure room.

BACKGROUND

There are many situations where a subject is in an enclosed environment, such as a room in a hospital, secure room in a prison or hospital, or even a home environment, where a duty of care is placed on an authority responsible for the subject. To comply with such duty of care requirements, it is conventional to monitor subjects in such environments. Such monitoring may comprise regular, scheduled visual checks by a member of staff and/or continuous video monitoring of the subject in the room. While such monitoring can be effective, difficulties can arise with the subject's condition changing quickly between scheduled checks, or with a lack of movement of the subject being misinterpreted. For example, a subject who is lying still on a bed or on the floor may be resting or asleep, or may have suffered a deterioration in health. Subjects who are under the influence of alcohol or drugs or suffering from a mental condition may behave in ways which are abnormal and difficult for staff observing them to interpret correctly. This increases the burden on staff as subjects must be checked individually, in person. It may also be necessary or useful to record the pattern of movement of a subject, e.g. how often they get out of bed at night, their speed, etc., as this can give an indication of their physical or mental state, but recording such activity manually is labour intensive.

It would therefore be useful to have a way of automatically monitoring the subject which provides an indication of their condition, e.g. state of health or activity level, and that can both record this and alert staff to those subjects needing attention.

Automatic monitoring of vital signs offers the possibility of mitigating some of these problems, but traditional contact-based vital signs sensors are restrictive and inconvenient, and some subjects may not co-operate with their use. Recent developments demonstrating that vital signs such as heart rate or breathing rate can be detected in video images of the human body, where the video images are obtained using a standard video camera, are of significant interest. For example Verkruysse et al., "Remote plethysmographic imaging using ambient light", Optics Express, 16 (26), 22 Dec. 2008, PP. 21434-21445 demonstrated that changes in reflectivity or transmittivity of the subject's skin caused by cardiac-synchronous variations in the volume of oxygenated blood in the skin capillaries, known as photoplethysmographic image or PPGi signals, could be detected in the video signal from a conventional consumer standard video camera where a human subject was illuminated under ambient light. This idea has been developed further in, for example, WO-A2-2013/027027, WO-A-2011/021128 and WO-A1-2015/049150 which aim to increase the reliability of the detection of the remote PPG signal.

The paper "Distance PPG: robust non-contact vital signs monitoring using a camera" by Mayank Kumar et al.; 6 Apr. 2015; Biomedical Optics Express 1565, 1 May 2015, Vol. 6 No. 5, discusses a method of combining skin-colour change signals from different tracked regions of a subject's face using a weighted average, where the weights depend on the blood perfusion and incident light density in the region to improve the signal-to-noise ratio of the camera-based estimate. It discusses the various challenges for camera-based non-contact vital sign monitoring and proposes that improvements in the signal-to-noise ratio of the camera-based estimates reduces the errors in vital sign estimation.

Many of the prior art techniques have been based on careful control of both the subject being monitored and the lighting conditions in the environment. Thus, although they claim success in detecting the heart rate or vital signs of the subject, in general the subjects were required to remain relatively still, the subjects were not obscured and the lighting conditions were kept relatively constant. These conditions are in general not true of real situations where lighting changes, e.g. with sunlight through a window, the subject moves or may become obscured, there may be confounding sources of movement such as other people, insects or equipment such as fans in the room, or movement from outside the room but which is visible through a window or that affects the lighting in the room.

Other techniques based on detecting fine movement associated with breathing or heart activity from a combination of movement and micro-blushes (PPGi) have also been proposed. In the health and security monitoring fields proposals have also been made for detecting and classifying the gross movement of subjects in a video image as dangerous or non-dangerous, for example the proposal for detecting clonic seizures as described in the paper "Real-time automated detection of clonic seizures in newborns" by Pisani et al.

Another common problem with such video image analysis is finding and tracking the subject in the video image. The human body is naturally deformable and the orientation of the subject with respect to the camera's view point can vary significantly. Also the subjects may be still, in which case motion-based detection and tracking can fail, or may move significantly or in unpredictable ways, which can be difficult for feature-based techniques. Even in a relatively simple visual scene, such as a single human subject in a fairly plain room (as may be found in care or secure institutions such as hospitals, care homes, detention centres or prisons), subjects may be covered with bedclothes, which can make them difficult to detect automatically, and actions such as throwing bedclothes across the room can cause image features which were previously associated with the subject to move across the image and thus confuse automatic analysis. Subjects mix periods of high activity and large movement with periods of relative immobility (seated or lying), will in general be clothed and have bedding to cover themselves. Thus, periods of inactivity while lying down, may coincide with the subject covering themselves partly or completely with bedding. Further, illumination may vary between daylight and artificial light and secure rooms are sometimes lit with visible artificial light and are sometimes completely dark, with infrared being the only illumination available. Other sources of regular or irregular movement may also appear in the scene being monitored—e.g. insects flying in, ventilation fans, domestic appliances.

Also, the arrangement of the video monitoring apparatus itself may cause difficulty for the video analysis. For safety reasons the video camera or cameras have to be positioned out of reach of the subject, normally high in a corner of the room. This means that the view of the subject tends to be compressed by perspective and the subject is only a relatively small fraction of the field of view. Further, because the monitoring has to continue in the dark (when the subject is asleep), it is normal to use a monochrome infrared camera, which means that techniques relying on full colour images do not work.

In the context of monitoring the health and welfare of subjects for whom an institution may have a duty of care, the reliability of the system in real conditions is paramount, otherwise the system cannot be relied upon as helping discharge the institution's duty of care.

Existing systems do not provide monitoring, including vital signs monitoring such as heart or breathing rate detection, which operates reliably in the face of these difficulties associated with the wide variety of poorly-controlled settings in which such monitoring may be used.

Similar problems of movement and variable illumination occur also in other fields such as fitness and health and well-being in the home, on a farm, in a zoo or elsewhere.

Being able to monitor a subject in these less controlled conditions and provide practically useful information would significantly improve the ability to monitor the well-being of such a subject and to comply with duty of care requirements, particularly in the health or security field. As with all monitoring systems, the primary need is to avoid excessive false alarming and also to avoid excessive under alarming. Excessive false alarming leads to monitoring systems being ignored by staff, or switched off. Excessive under alarming leads to a lack of trust in the system and does not meet the basic requirements of the monitoring system.

SUMMARY

One aspect of the present invention therefore provides a method of monitoring a human or animal subject comprising the steps of: capturing a video image of the subject consisting of a time series of image frames each frame comprising a pixel array of image intensity values; and analysing the video image to determine automatically one or more vital signs of the subject; wherein the step of determining automatically one or more vital signs of the subject comprises: analysing the image to detect a plurality of signals each comprising the variation in image intensity with time at each of a respective plurality of positions in the image, determining a first plurality of signal quality indices of the signals and retaining only those signals whose signal quality indices are above a predetermined threshold, analysing the retained signals in a multi-dimensional component analysis to obtain components thereof and retaining a predetermined number of the strongest components, determining a second plurality of signal quality indices of the retained components, selecting amongst the retained components on the basis of the second plurality of signal quality indices, determining the frequency of the selected components, and outputting a vital sign estimate based on said determined frequencies.

Further stages which thin out the number of signals for the downstream processing steps, i.e. of analysing signal quality indices and retaining only those whose signal quality indices are above a predetermined threshold, may be added before or after the multi-dimensional component analysis.

Each of said plurality of signals may comprise the variation in intensity at a plurality of pixels in a local neighbourhood in each of said image frames whose intensity values are combined together to form one of said plurality of signals The pixels in the local neighbourhood may be pixels that are adjacent, or within a predetermined distance.

Said plurality of positions in the image may be positions in the image at which subject movement has been detected.

The method may further comprise the step of frequency filtering each of said plurality of signals to exclude those outside predetermined expected or allowed physiological range for said one or more vital signs.

The method may further comprise the step of scaling intensities in the image as mentioned above, e.g. by calculating the logarithm of said image intensity values to form a logarithm image, or using some other scaling function, and said step of analysing the image is performed on the resulting image.

Said first plurality of signal quality indices may comprise measures of one or more of periodicity, such as peak consistency and amplitude consistency. These indices are relatively quick to calculate and do not require large processing resources.

The step of analysing each of the retained signals to find the components thereof may comprise a multi-dimensional component analysis to decompose the signals into their components, examples being principal components analysis, ICA (Independent Component Analysis).

The second plurality of signal quality indices may comprise measures of one or more of: peak consistency, amplitude consistency, location in the image, distance between signals in the image, and variability. The method may further comprise the step of determining from said second plurality of signal quality indices a confidence value for each of said retained components and using said confidence value in said selecting step. Thus more signal quality indices, potentially including ones which require more processing resources are carried out on a significantly reduced number of signals, increasing the efficiency of the method.

The selecting step may comprise weighting said retained components by said confidence value and updating a prior estimate of said one or more vital signs by said weighted components. The method may further comprise the step of down-weighting said prior estimate of said one or more vital signs by a predetermined amount before updating it with said weighted components. Thus a running estimate of vital signs is maintained, based on previous estimates and their confidence, and the current estimates, with the influence of previous estimates decaying with time.

The method may further comprise the step of detecting the amount of subject movement in the image and varying said predetermined amount, e.g. in dependence upon the detected amount of subject movement. Thus the influence of previous estimates on the running estimate may decay more quickly in some circumstances. One example is where a lot of movement is detected in the image.

The step of determining from said second plurality of signal quality indices a confidence value for each of said retained components may conducted by a machine learning technique such as a trained artificial neural network. Other ways of calculating a confidence value are also possible, such as logistic regression, a non-linear combination of the components and their SQIs, or other machine learning techniques.

Another aspect of the invention, which may be combined with any of the above aspects, provides a method of monitoring a human or animal subject comprising the steps of: capturing a video image of the subject consisting of a time series of image frames each frame comprising a pixel array of image intensity values; analysing the video image to determine automatically one or more regions of interest in the image in which variations in the image intensity contain signals representative of the physiological state of the subject, said signals comprising at least one vital sign and subject movement; analysing the intensity values in the regions of interest to determine subject movement and at least one vital sign of the subject; wherein the step of determining automatically one or more regions of interest in the image comprises analysing the image to measure the amount of variation in image intensity with time at each of a plurality of positions in the image, and selecting as regions of interest those positions at which the amount of variation in image intensity with time is above a predetermined threshold.

Each of said plurality of positions may comprise at least one pixel of the image, e.g. a plurality of neighbouring but not necessarily contiguous pixels in each frame, or pixels from nearby or in a local area of the image, whose intensity values are combined together, for example by averaging.

The number of neighbouring pixels whose intensity values are combined together may be set to a first value for determining subject movement and to a second value, different from said first value, for determining said at least one vital sign. The second value may be set in dependence upon the vital sign being determined.

The video image may be temporally resized before analysis by combining together a plurality of successive frames of the video image. The number of frames that are combined together may be set to a first value if subject movement is being determined and to a second value, different from said first value, if a respiration rate of said subject is being determined.

The spatial and/or temporal resizing are advantageous if the data processing burden needs to be reduced.

Predetermined areas of said video image may be masked out. Such areas may be defined, e.g. on set-up, by an operator and may correspond to image areas that are expected to include confounding sources of image intensity variation or movement.

In one embodiment a function may be applied to the image intensities that magnifies lower intensities and reduces the prominence of greater intensities to produce a non-linearly-scaled image, and the step of measuring the amount of variation in image intensity with time is conducted upon on the resultant image. One example of this is to take the logarithm of the image intensities to form a logarithm image, and image analysis is conducted upon the logarithm image. Other scaling functions such as taking the square root of the intensities may be used.

The step of analysing the image to measure the amount of variation in image intensity with time at each of a plurality of positions in the image may comprise analysing the video image to automatically determine the amount of movement by detecting spatial intensity variations representing edges in the image to form an edge image; and measuring the variation with time of the edge image at each of a plurality of positions in the image to form a respective plurality of movement signals. An edge image is one where edges in the image are enhanced, i.e. have greater intensity. One way of achieving this is to calculate the derivative (first or a higher derivative) of the image, e.g. by applying a kernel convolution.

The method may further comprise grouping the movement signals into a plurality of groups according to their position in the image, quantifying the variability in each of the movement signals and forming for each group a representative single movement signal, determining whether the variability of the representative movement signal is above a predetermined threshold, and determining movement as being present at that position in the image if the variability of the retained movement signal is above the predetermined threshold.

The step of detecting spatial intensity variations representing edges in the image to form an edge image may comprise applying a kernel convolution to each frame of the image, the kernel convolution combining the intensities of a plurality of neighbouring pixels in the frame to detect edges in the image.

The method may further comprise the step of detecting global intensity variations in the image and de-correlating the measured amount of variation in image intensity with time from the detected global intensity variations. The step of detecting global intensity variations may comprise detecting variations in image intensity in predefined areas of the image, e.g. by detecting principal components in the variations in image intensity, and retaining as representative of global intensity variations only those principal components whose variability is above a predetermined threshold.

Another aspect of the invention, which may be combined with any of the above aspects, provides Another aspect of the invention, which may be combined with any of the above aspects, provides a method of monitoring a human or animal subject comprising the steps of: capturing a video image of the subject consisting of a time series of image frames each frame comprising a pixel array of image intensity values; analysing the video image to detect signals comprising temporal variations in the image intensity representative of movement of the subject; and outputting an indication of the movement of the subject; wherein the step of analysing the video image to detect signals comprising temporal variations in the image intensity representative of movement of the subject comprises: measuring the variation with time of the image intensity at each of a plurality of positions in the image to form a respective plurality of movement signals; grouping the movement signals into a plurality of groups according to their position in the image, quantifying the variability in each of the movement signals and forming for each group a representative single movement signal, determining whether the variability of the representative movement signal is above a predetermined threshold, and determining movement as being present at that position in the image if the variability of the retained movement signal is above the predetermined threshold.

The step of measuring the variation with time of the image intensity at each of a plurality of positions in the image may comprise detecting spatial intensity variations representing edges in the image to form an edge image; and measuring the variation with time of the edge image at each of a plurality of positions in the image to form the respective plurality of movement signals.

The step of detecting spatial intensity variations representing edges in the image to form an edge image may comprise applying a kernel convolution to each frame of the image, the kernel convolution combining the intensities of a plurality of neighbouring pixels in the frame to detect edges in the image.

The method may further comprise the step of applying a function to the image intensities that magnifies lower intensities and reduces the prominence of greater intensities to produce a non-linearly-scaled image, and the step of measuring the amount of variation in image intensity with time is conducted upon on the resultant image. An example is to determine the logarithm of the image intensities in each frame to form a logarithm image and wherein said step of analysing is conducted upon the logarithm image.

The step of forming for each group a representative single movement signal may comprise retaining for each group a predetermined ordinal one of the movement signals ordered by their variability, e.g. the fifth to the fifteenth largest, e.g. the tenth largest, determining whether the amplitude variability of the retained movement signals are above a predetermined threshold, and determining movement as being present at that position in the image if the variability of the retained movement signal is above the predetermined threshold.

Each of said plurality of positions may comprise at least one pixel of the image. Optionally the intensity values of a plurality of neighbouring pixels are combined together, e.g. by averaging or taking a representative one, to form a spatially resized image upon which said analysis step is conducted.

A temporally resized image upon which said analysis step is conducted may be formed by combining together corresponding pixel values in a plurality of successive frames of the video image.

Predetermined areas of said video image may be masked out. The method may further comprise the step of detecting global intensity variations in the image and de-correlating them from the image. The step of detecting global intensity variations may comprise detecting variations in image intensity in predefined areas of the image. The step of detecting global intensity variations may comprise detecting principal components in the variations in image intensity, and retaining as representative of global intensity variations only those principal components whose variability is above a predetermined threshold.

Another aspect of the invention, which may be combined with any of the above aspects, provides a method of monitoring a human or animal subject comprising the steps of: capturing a video image of the subject consisting of a time series of image frames each frame comprising a pixel array of image intensity values; analysing the video image to determine automatically at least one of subject movement or at least one vital sign of the subject by analysing the image to detect a plurality of signals each comprising the variation in image intensity with time at each of a respective plurality of positions in the image; detecting global intensity variations in the image and de-correlating the detected global intensity variations from said plurality of signals; wherein the step of detecting global intensity variations comprises detecting variations in image intensity in predefined areas of the image.

The image intensity may be spatially averaged in each of the predefined areas of the image.

The step of detecting global intensity variations may comprise detecting components in the variations in image intensity, and retaining as representative of global intensity variations only those components whose variability is above a predetermined threshold.

The method may further comprise the step, after de-correlating for global intensity variations, of rescaling the plurality of signals in accordance with the number of retained components. This may be achieved by dividing each pixel value in the time window by a number based on the number of retained components.

The components are determined by principal components analysis or another special analysis technique.

Each of said plurality of positions may comprise at least one pixel of the image. For example, each of said plurality of positions comprises a plurality of neighbouring pixels whose intensity values are combined together, e.g. by averaging or taking a representative one.

The number of neighbouring pixels whose intensity values are combined together may be set to a first value for determining subject movement and to a second value, different from said first value, for determining said at least one vital sign. The second value may be set in dependence upon the vital sign being determined.

The video image may be temporally resized before the analysing steps by combining together a plurality of successive frames of the video image. The number of frames that are combined together may be set to a first value if subject movement is being determined and to a second value, different from said first value, if a respiration rate of said subject is being determined.

Predetermined areas of said video image may be masked out.

The logarithm of the image intensities may be taken to form a logarithm image, and the step of analysing the image to detect said plurality of signals may be conducted upon on the logarithm image.

The method may further comprise detecting spatial intensity variations representing edges in the image to form a derivative image; measuring the variation with time of the derivative image at each of a plurality of positions in the image to form a respective plurality of movement signals.

The methods of the different aspects of the invention may further comprise the step of compensating the image for pixel noise by down-weighting signals having low image intensity. The method may further comprise applying a saturation mask to mask out image areas whose image intensity is above a predetermined maximum brightness or below a predetermined minimum brightness.

One or more of the above aspects of the invention and optional or preferred features may be combined together.

The video camera may be a standard digital video camera so that the video image sequence is a conventional frame sequence with each frame comprising a spatial array of pixels of varying image intensities and/or colours. The camera may be monochrome or may be a colour camera providing pixel intensities in the red, green and blue channels.

The video image sequence may be time-windowed, i.e. divided into batches of successive frames for processing, and the analysis steps are conducted on successive time windows, with an output for each time window. The time windows may be of different length depending on the target of the analysis, e.g. different time windows for detecting movement, breathing rate or heart rate. For example windows of 120, 180 or 600 frames, corresponding to 6, 9 or 30 seconds at 20 frames per second, may be used respectively for movement, heart rate and breathing rate analysis. Successive time windows may be overlapping, for example by 1 second, resulting in an output each second, that output being based on the frames forming the time window.

The invention may also be embodied in a computer program for processing a captured video image sequence in accordance with the invention and for outputting the results on a display. Such a computer program may run on a general purpose computer of conventional type or on a dedicated video processor.

DRAWINGS

The invention will be further described by way of non-limitative example with reference to the accompanying drawings in which:

FIG. 1 schematically illustrates a room containing a subject under monitoring in accordance with an embodiment of the invention;

Figure 4:
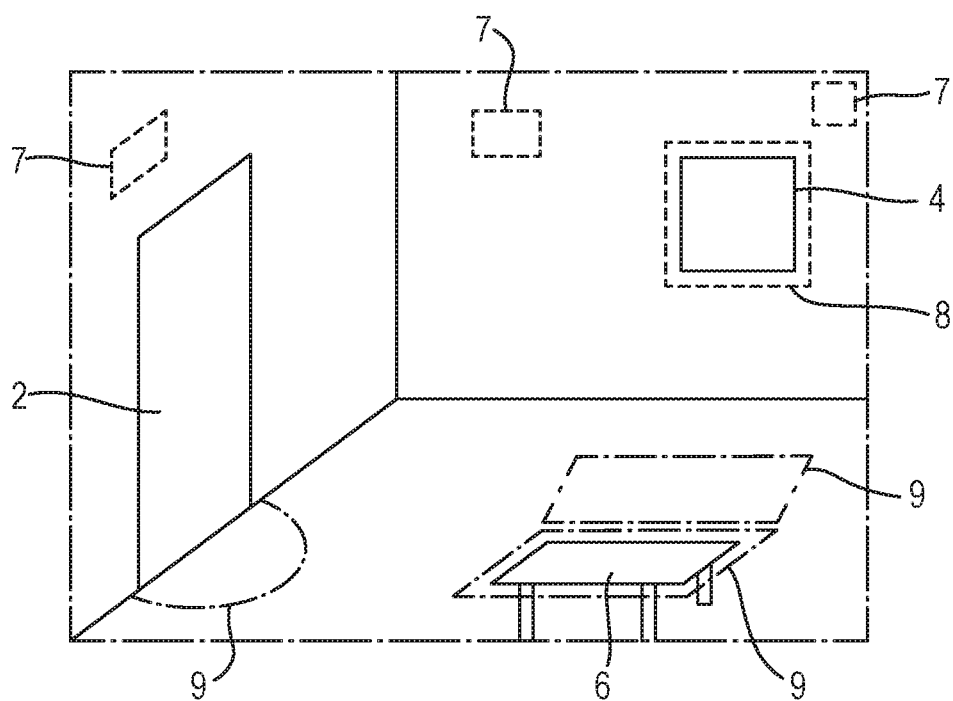
Figure 5:
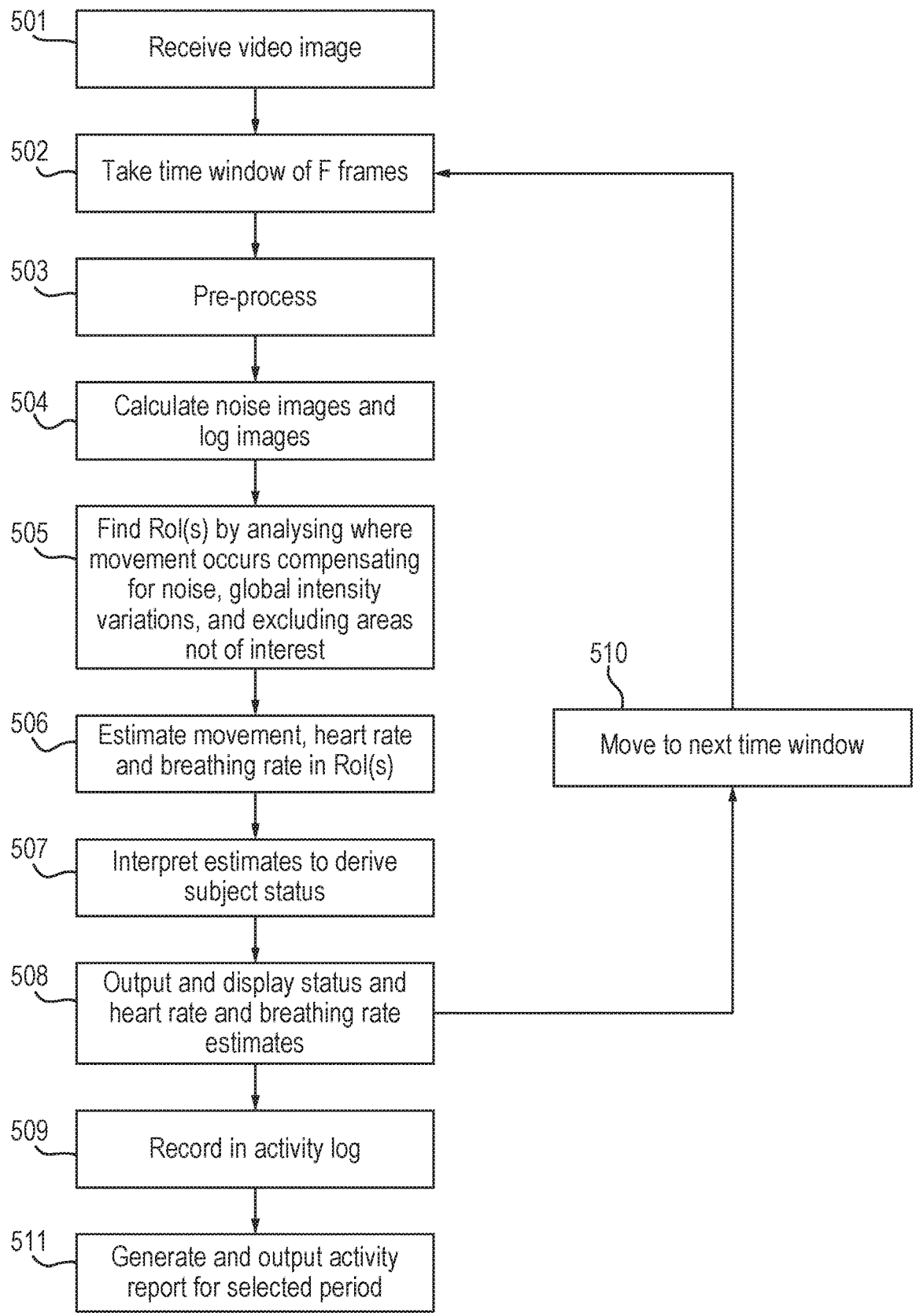
Figure 6:
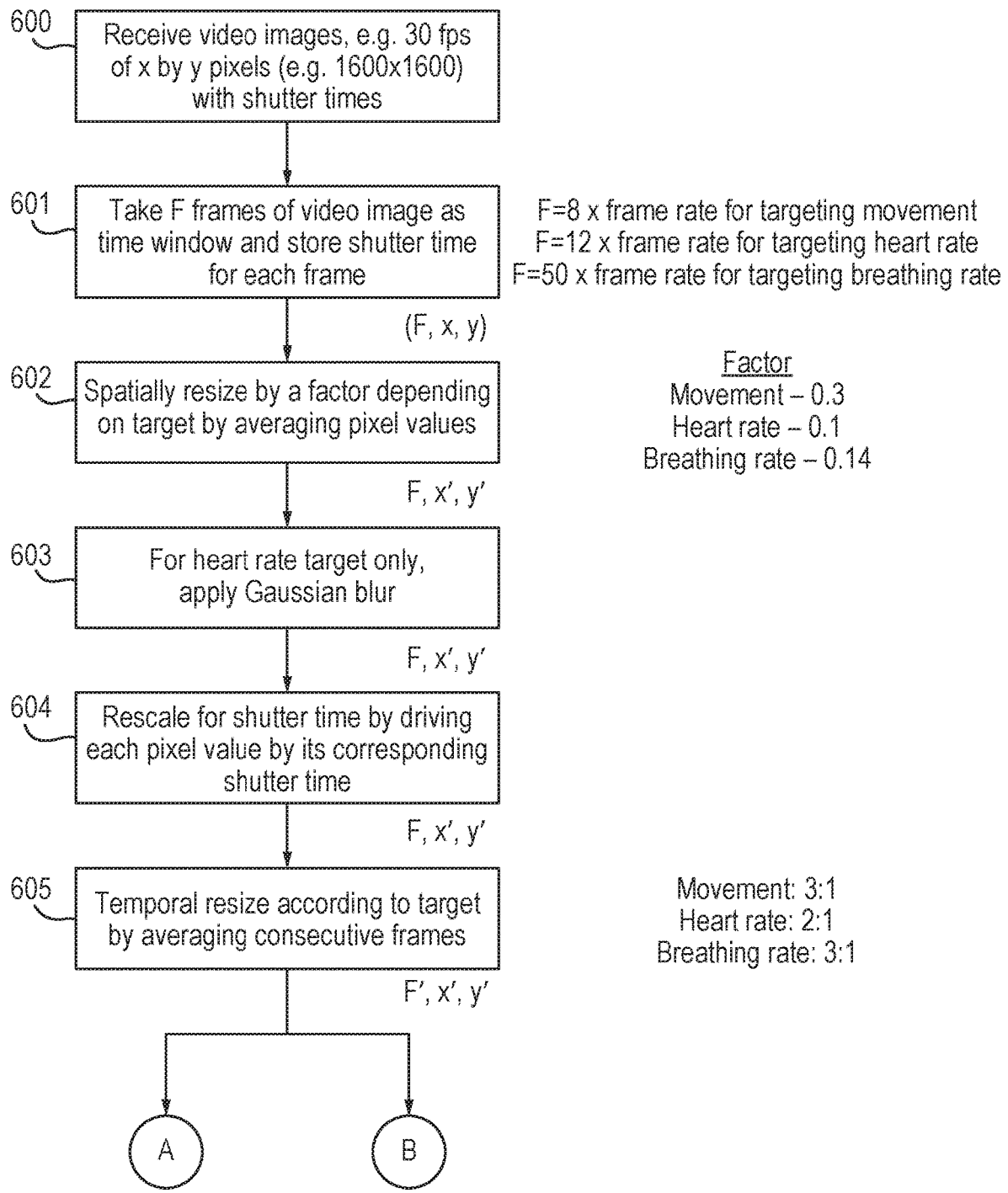
Figure 7:
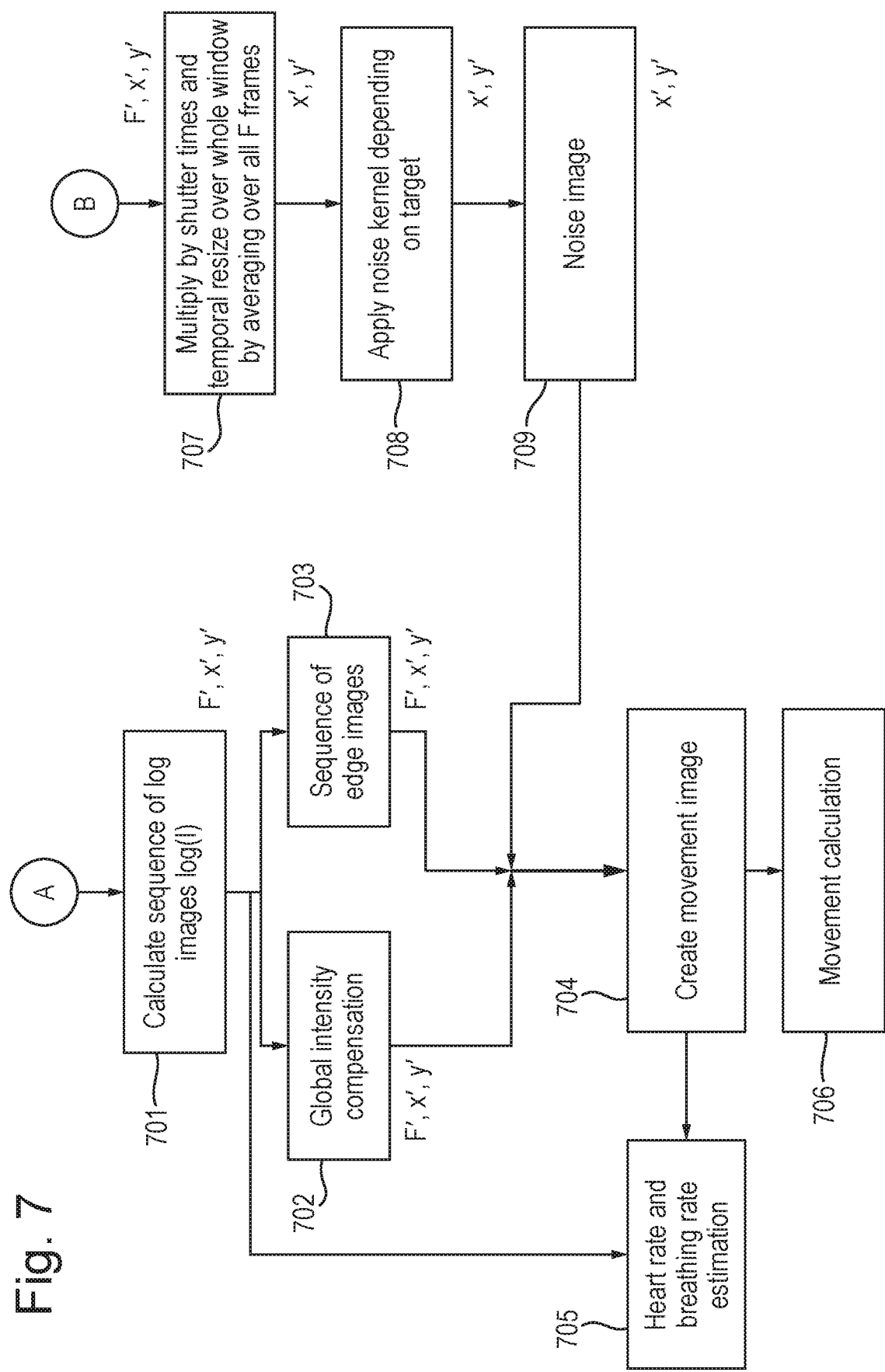
Figure 8:
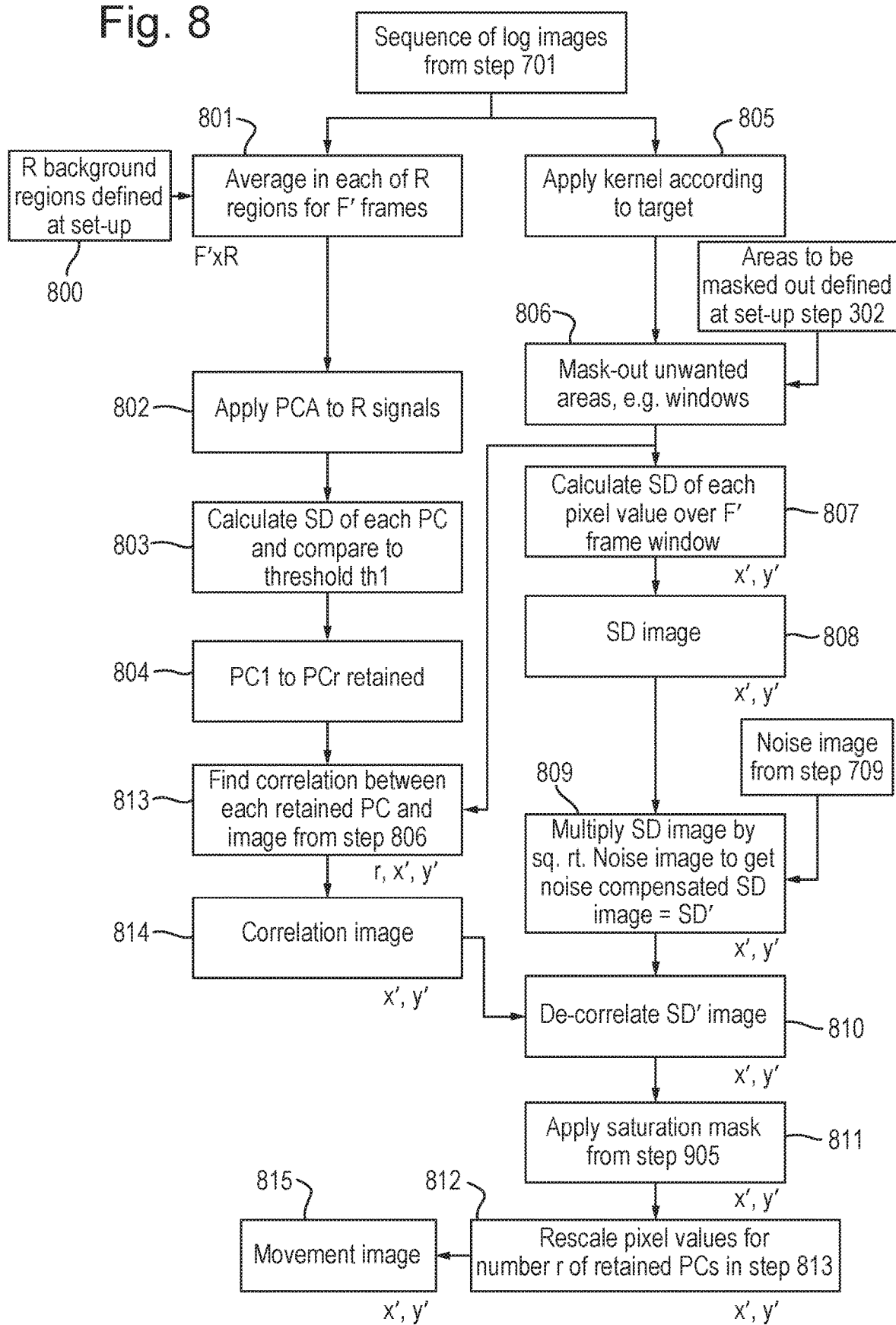
Figure 9:
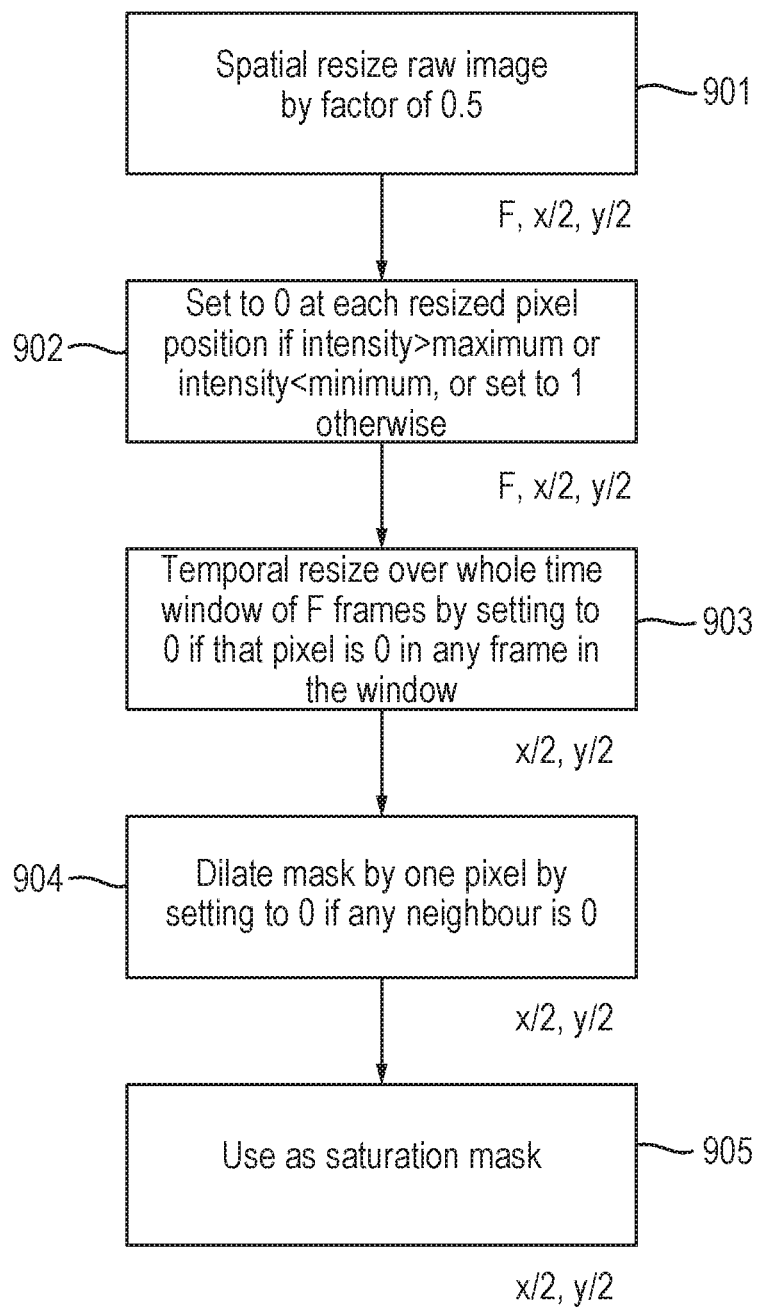
Figure 10:
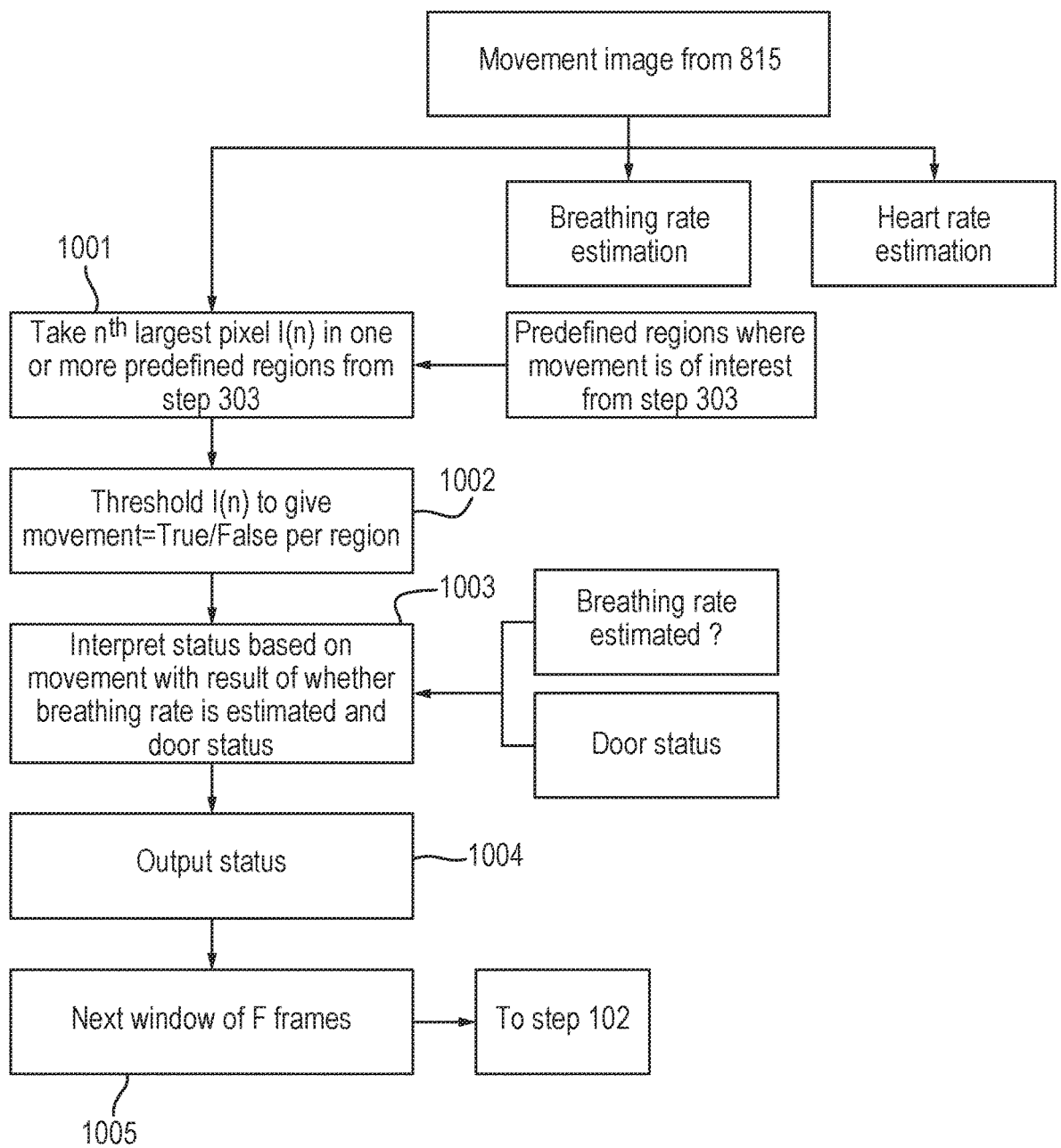
Figure 11:
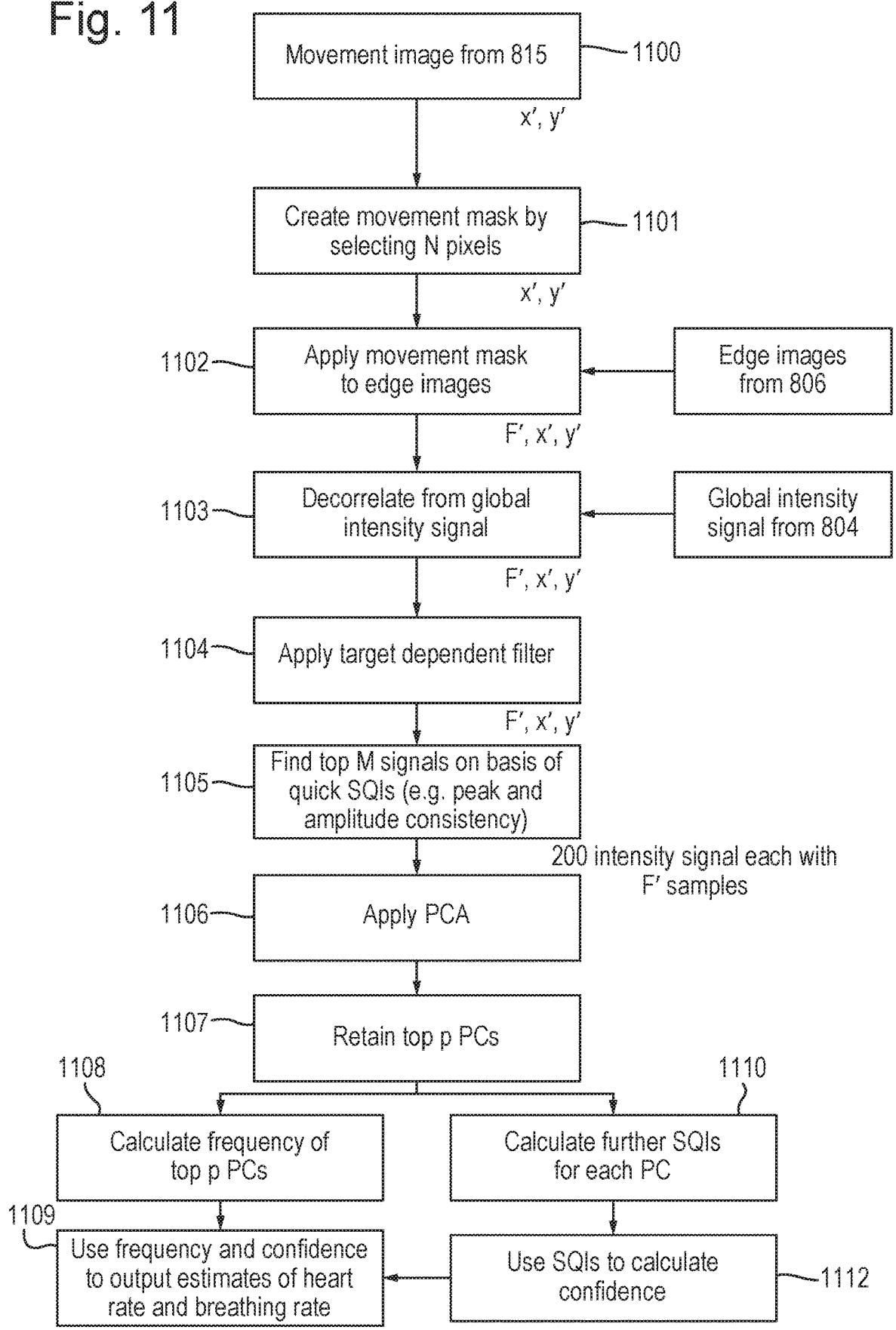
Figure 12:
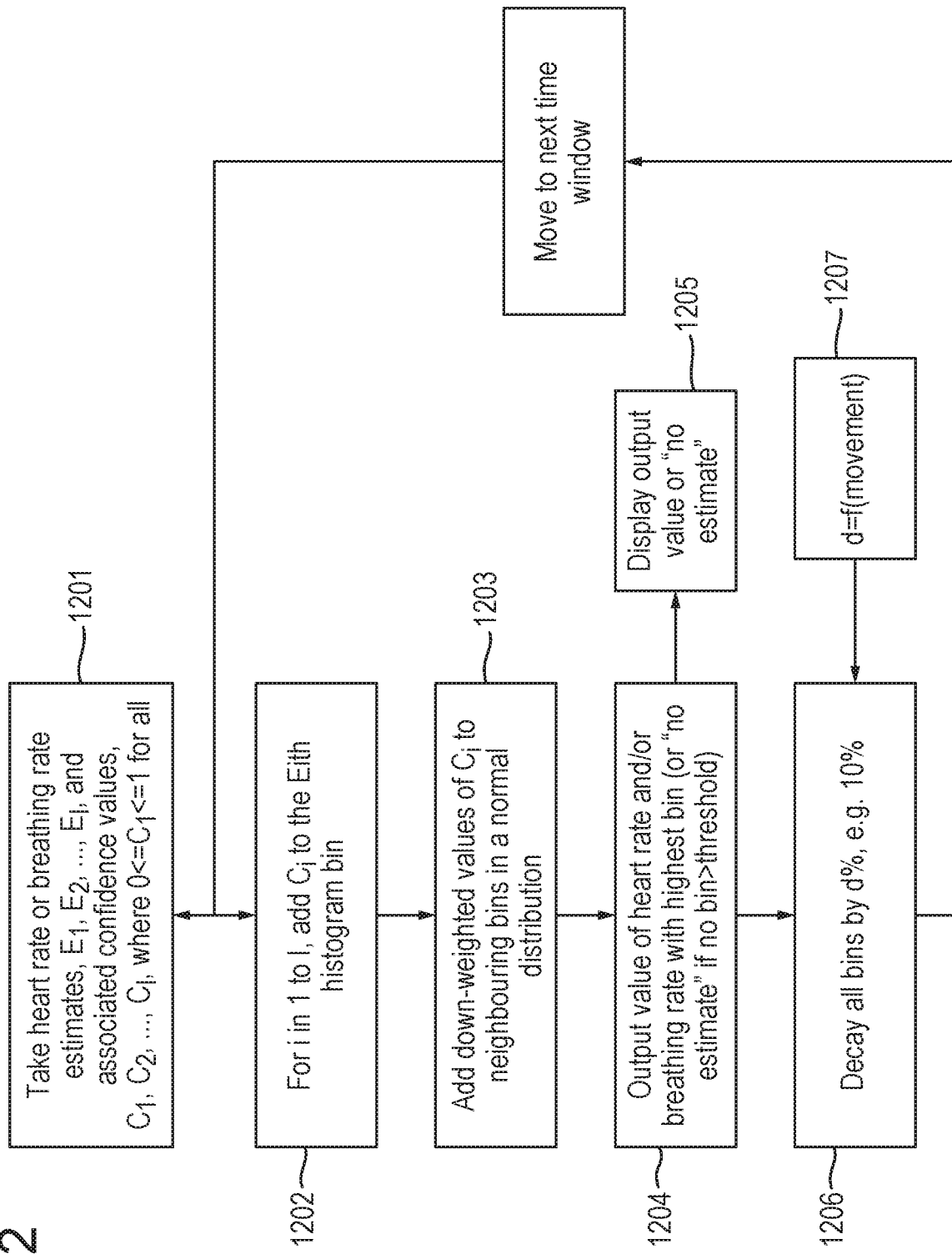
Figure 13:
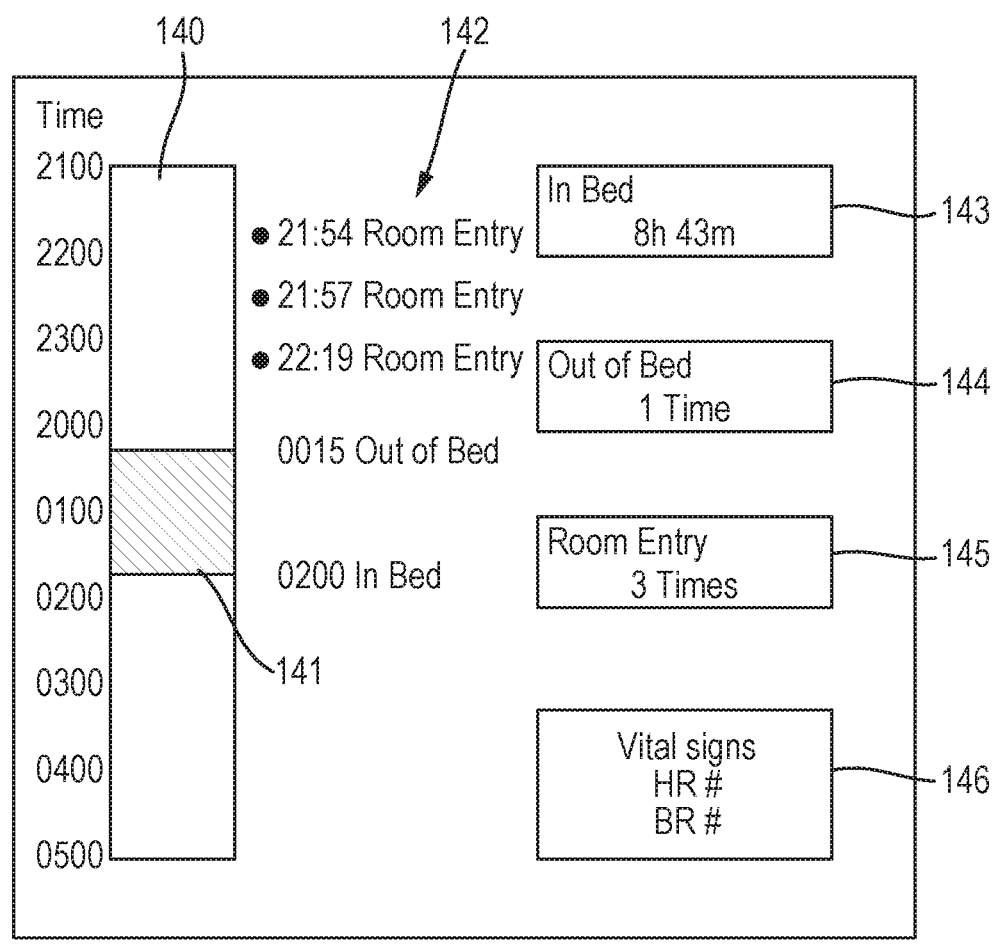

FIG. 4 schematically illustrates an example image frame of a video image in one embodiment of the invention;

FIG. 5 is a flow diagram of the video signal acquisition and analysis in one embodiment of the invention;

FIG. 6 is a flow diagram of the video signal pre-processing in one embodiment of the invention;

FIG. 7 is a flow diagram of part of the video signal processing in one embodiment of the invention;

FIG. 8 is a flow diagram of part of the video signal processing in one embodiment of the invention;

FIG. 9 is a flow diagram of part of the video signal processing to form a saturation mask in one embodiment of the invention;

FIG. 10 is a flow diagram of part of the video signal processing to detect movement and interpret it in one embodiment of the invention;

FIG. 11 is a flow diagram of part of the video signal processing for estimation of heart rate and breathing rate in one embodiment of the invention;

FIG. 12 is a flow diagram of part of the video signal processing for estimation of heart rate and breathing rate in one embodiment of the invention;

FIG. 13 schematically illustrates a report obtainable with one embodiment of the invention.

DETAILED DESCRIPTION

Figure 1:
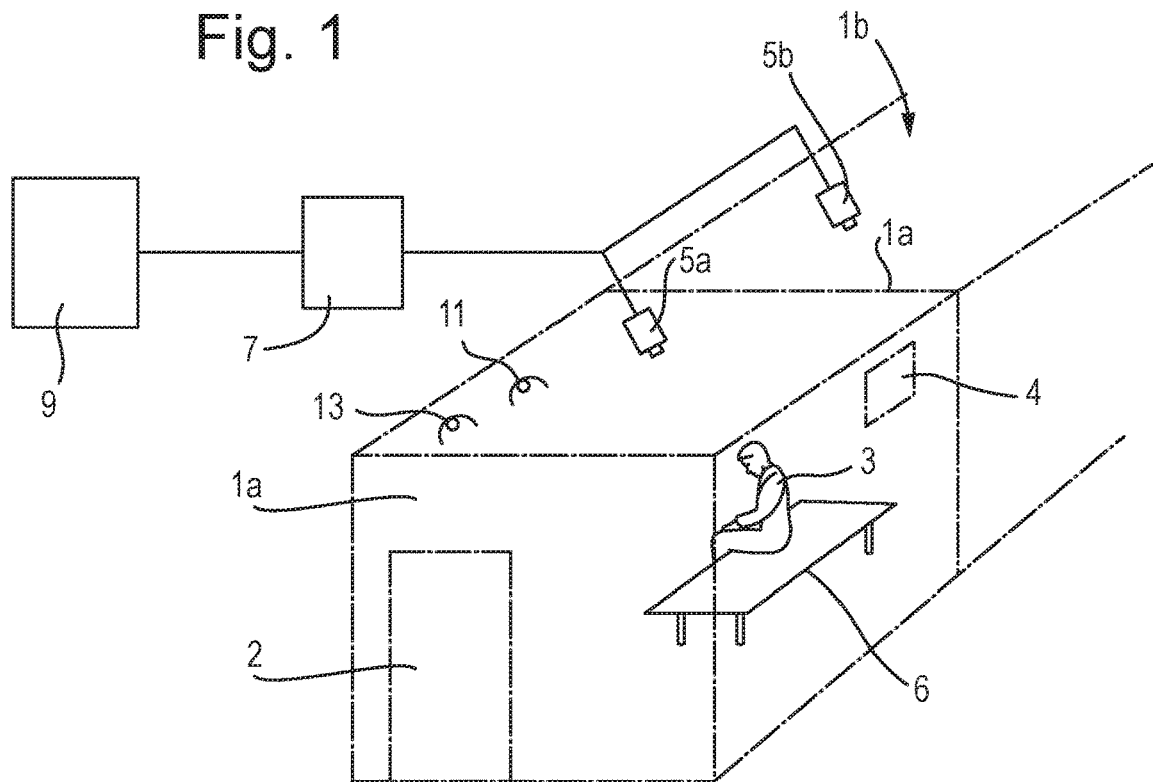

FIG. 1 schematically illustrates an apparatus in accordance with an embodiment of the invention being used to monitor a subject 3 in a room 1a. The room 1a can be a secure room such as a cell in a police station or prison or some other detention facility, or could be a room in a hospital or other care facility such as a care home, sheltered accommodation, the subject's own home or an environment used to shelter animals. It may be one of plural rooms being monitored as indicated by the neighbouring room 1b. The subject 3 is monitored by a video camera 5a whose output is processed by a video signal processor 7 and the results of the analysis are displayed on a display 9 which is visible to staff of the facility. The video signal processor 7 receives inputs from the video cameras 5b in other rooms. The video signal processor 7 may be a dedicated signal processor or a programmed general purpose computer. The rooms may be naturally lit or may be artificially illuminated using a visible light source 11 or infrared light source 13 and include a door 2 and may include one or more windows 4. Furniture, such as a bed 6, may be present.

The video camera 5a (b) is a standard digital video camera outputting video data in the form of a sequence of image frames, each frame being a pixel array of intensities in either monochrome or red, green, blue channels. The red, green and blue channels also give a response in the infrared range allowing the production of an infra-red (IR) image useful when the room is dark. Video cameras of this type typically output the signal at thirty frames per second, though of course different frame rates are possible as long as the rate is greater than the minimum required to estimate the highest frequencies in the signal being analysed.

The display 9 preferably displays the video image of the rooms and also displays information regarding the physiological state, e.g. health or safety, of the subject 3. This information is preferably one or more of:

Whether movement is present.
Whether vital signs are being acquired.
Whether the subject is judged to be safe.
Current values of estimated vital signs such as heart rate and breathing rate.
Whether no vital signs have been detected and the time for which no vital signs have been detected.
A no movement and no vital signs alert or alarm.

Staff monitoring the subject by way of the display 9 can therefore tell at any given time whether the subject can be considered safe, for example because they are moving or because the vital signs are being detected and are in a physiologically normal range, or whether the system is unable to detect vital signs but safe movement is detected (and for how long that situation has persisted), or that no vital signs and no movement is present, in which case an alert is generated instructing staff to check the subject. If the lack of vital signs detection persists for more than a configurable amount of time an audio and/or visual alert may be generated to call on staff to check the subject. Alerts can included a range of electronic notification methods including, but not limited to, automated telephone message, pager, SMS, as well as indication on the display 9 with the alert containing the condition and location of the subject and the condition being alerted.

As well as providing live monitoring information the system may also record and provide a summary report of the status of the subject 3, such as activity level by time through the day, vital signs and any alerts raised during predetermined periods, e.g. daily, weekly, monthly, and/or for the complete period the subject is in the room.

Figure 2:
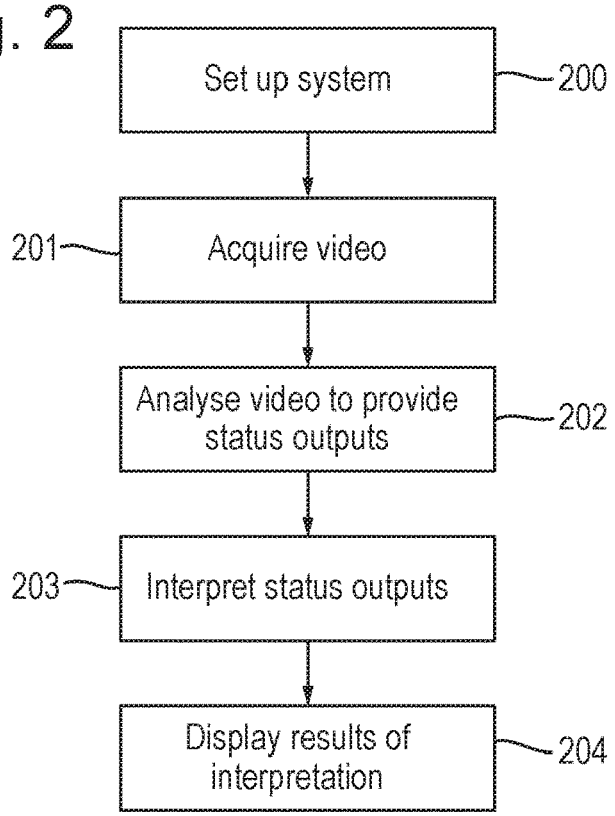
FIG. 2 is a flow diagram of the overall processing in one embodiment of the invention.

FIG. 2 is a flow diagram showing the overall processing by the video processor 7 in one embodiment of the invention. Firstly, in step 200 the system is set up by an operator. This involves not only physically positioning or checking the cameras 5a, 5b, but also viewing the images obtained by the video cameras and defining certain regions which will be used by the video signal processing as will be described later. Such regions may include, for example, background regions which are parts of the image that are not expected to include an image of the subject 3, areas to be masked-out such as images of undesired features such as the window 4, and specific areas where movement is of particular interest because they are expected to be occupied by the subject 3. Such areas may be on or next to furniture such as bed 6, areas near the door 2, or areas near to other internal doors (for example in a care home, a subject's room may adjoin a bathroom and it may be of interest to detect movement of the subject through a region next to the door of the bathroom). In the case of application to animal habitats such areas may be sleeping areas or feeding or drinking areas of an animal enclosure. The subsequent normal operation of the system is then generally illustrated by steps 201-204. In step 201 the video image from the camera or cameras 5a, b is acquired by the video signal processor 7 and in step 202 the video image is analysed by the video signal processor 7 to provide status outputs relating to the physiological state of the subject 3. The steps of acquiring and analysing the video image continue while the system is in operation. The status outputs from the analysis of the video images are interpreted by the video signal processor 7 in step 203 and displayed on display 9 in step 204. Steps 202 to 204 will be described in more detail below.

Figure 3:
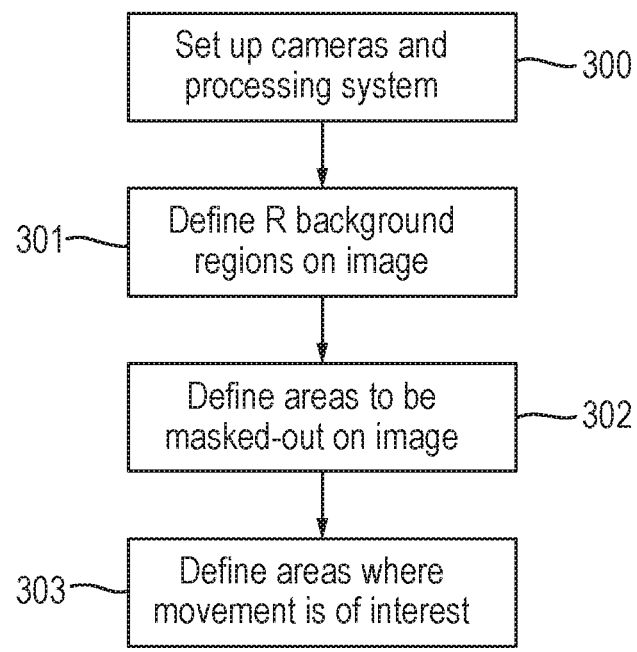
FIG. 3 is a flow diagram of the system set-up steps in one embodiment of the invention.

FIGS. 3 and 4 illustrate in more detail one example of the set-up step 200 of FIG. 2. In step 300 the video cameras 5a, b are set up and connected to the video signal processor 7, or an existing set-up and connection is checked, and video images of the rooms are viewed on the display 9. In step 301, for each of the rooms 1a, 1b, regions 7 in the image are defined which correspond to background regions where the subject 3 is not expected to be present. These will be used later in the detection of global intensity variations, such as changes in sunlight or artificial light, which are unrelated to the subject's condition. Examples including regions on the ceiling or high on the walls. Typically at least three such background regions are defined.

In step 302 areas 8 of the image are defined which should be masked-out and excluded from analysis. These are typically areas which may include a source of movement or lighting change which is not related to the activity of the subject. An example would be the window 4, where the camera may be able to see movements from outside the room, or lighting changes from outside. Other examples would be sources of confounding movement in the room such as curtains, mirrors, hatches connecting to other rooms, domestic appliances (e.g. ventilation fans).

In step 303 certain areas 9 of the image are defined where subject movement is of particular interest. These areas may include an area around the door 2, an area next to the bed 6, an area on the bed 6. Where the room includes interconnecting doors, further areas 9 may be defined near them, and further areas 9 may be defined on and near other items of furniture such as desks, chairs, tables etc.

FIG. 5 breaks down into more detail steps 202 to 204 of FIG. 2 relating to the processing of the video signal. The same general form of process flow is used by the video signal processor 7 to analyse the video signal to detect three targets—subject movement, subject's breathing rate and subject's heart rate, but certain parameters in the process, e.g. the length of the time window analysed and certain filtering parameters, differ between the three targets. In the following description, for conciseness, the process flow will be described once, noting where there are differences for the three targets of the analysis, it being understood that the video signal processor is in practice running the three analyses in parallel.

In step 501 the video image from the camera or cameras 5a, b is received by the video signal processor 7. In step 502 the video signal processor 7 then takes a time window of F frames of the video signal. As will be discussed in more detail below, the length of the time window, i.e. the number of frames F taken for processing, depends on whether the analysis is seeking to detect and quantify movement of the subject, to detect a heart rate of the subject or to detect a breathing rate of the subject. Successive overlapping time windows will be defined and each is processed separately. The overlap may be, for example, from 0.5 to 5 seconds, more preferably 0.9 to 1.1 seconds, e.g. 1 second.

In step 503 the image is pre-processed as discussed in more detail below, for example to compensate for varying shutter times of the camera and to spatially and temporally resize the image. Other pre-processing steps may be present, such as applying Gaussian blurring. In step 504 a noise image representing the amount of expected pixel noise is calculated and, in parallel, the logarithm of the intensity at each pixel position in the resized image is taken to produce a sequence of logarithm images.

In step 505 the sequence of logarithm images is processed to detect areas of the image where most subject movement appears to be occurring. These areas constitute regions of interest for subsequent analysis. An aim of this embodiment is to find such regions of interest automatically and quickly, so that they can be found automatically in real time without requiring further operator input after the initial set-up.

Having located the regions of interest and compensated for noise and the effects of global intensity variations such as changes in sunlight, in step 506 the subject movement, heart rate and breathing rate are obtained from the regions of interest as will be explained in more detail below. The subject movement is assessed as being present or not present in each of the areas 9 that were predefined in the system set-up and heart rate and breathing rate estimates are obtained by component analysis of the image signals in the regions of interest identified in step 505. In step 507 the movement determination and vital sign estimates are interpreted automatically to determine the status of the subject. In step 508 the current status of the subject is output and the heart rate and breathing rate estimates are also output and these are displayed on display 9. The status of the subject and the heart rate and breathing rate estimates may be recorded in an activity log in step 509 and the process then returns to process the next overlapping time window of F frames in step 510.

FIG. 6 illustrates an example of the pre-processing 503 in more detail. In step 600 the video image is received. Typically a video image will consist of a time series of image frames, each frame comprising a pixel array of image intensity values. Typically the frame rate may be 30 frames per second of frames with a 1600×1600 pixel array of 12 bit intensity values. Each frame will also be associated with a shutter time corresponding to the image acquisition time and this is typically automatically controlled by the camera to achieve a consistent exposure.

In step 601 a time window of F frames of the video image are taken. As mentioned above the value of F depends on the target of the image analysis. This embodiment of video imaging processing has three targets, namely the detection of subject movement (for example gross movement), estimation of the subject's breathing rate (which may be characterised as fine movement), and estimation of the subject's heart rate which will be obtained on the basis of the photoplethysmographic signal in the image). In this example, to target the subject's movement the time window is set to 8 seconds and thus F is eight times the frame rate, to target heart rate estimation the time window is set to 12 seconds and thus F equals twelve times the frame rate, and for breathing rate estimation the time window is 50 seconds and thus F equals fifty times the frame rate. In different embodiments different length time windows may be taken for each of these targets and thus the particular value of F may be varied. For example, to detect movement the time window may be of 5 to 10 seconds, for detecting the heart rate the time window may be of 5 to 15 seconds, and for detecting breathing rate the time window may be of 20 to 60 seconds. The particular values are not essential to the invention but the breathing rate time window is generally selected to be longer than that for movement detection or heart rate estimation and the exact choice is a compromise between the frequency range to be detected, and the desired speed of reaction of the estimation to changes in frequency.

In the following processing, the original image may be processed by various operations on the intensity values, including blurring, averaging, kernel convolution, and rescaling the image to reduce the number of pixels. The term image will be used to describe not only the original raw image from the video camera, but also the rescaled array of processed values each associated with a particular position, and the new value at each position will still be referred to as a pixel value, though each such processed and rescaled pixel value will have been derived from several pixels in the original (raw) image and thus be representative of a larger area of the original image than the original pixels. The variation with time of the intensity at a particular position, i.e. the temporal variation of each pixel value through the time window, whether original/raw or processed and rescaled, can be taken together to form a time varying signal, which will have one sample per frame and a length equal to the duration of the time window. Thus if each frame is of x,y pixels, the time window would produce x×y such signals.

In step 602, in order to reduce subsequent processing burdens, each of the image frames is spatially resized by a factor depending on the target of analysis, by averaging together neighbouring pixel values in the frame. Where the target of analysis is movement detection the spatial resizing is by a factor of 0.3, where the target of the analysis is heart rate estimation the spatial resizing is by a factor of 0.1 and where the target of the analysis is breathing rate estimation, the spatial resizing is by a factor of 0.14. Thus the time windowed video image is now a set of F frames each of a reduced number x', y' of pixels. The factor by which the image frames are resized may be varied depending on the downstream processing capability. Thus more of a reduction may be required if the processing capability is lower, but at the expense of accuracy.

In step 603, in the case only of analysing the video image to estimate heart rate, a Gaussian blur is applied. This involves applying a kernel convolution with a Gaussian profile. Typical parameters for the Gaussian blur are a kernel size of 5 pixels and sigma 0.8. Gaussian blurring is not applied in the case of analysing the video image for movement or breathing rate.

In step 604 the resulting image is compensated for shutter time variations by dividing each pixel value by the shutter time for the corresponding frame. Then in step 605 the images are temporally resized by a factor which, again, is set in accordance with the analysis target, by averaging a number of consecutive frames together. In this embodiment, for movement detection and breathing rate estimation three consecutive frames are averaged into one, and for heart rate estimation two adjacent frames are averaged into one. This therefore results in a pre-processed set of F' frames each of x' by y' pixels.

The pre-processed video images are then passed to two streams of processing as illustrated in FIG. 7.

In a first stream A, in step 701 the logarithm of each of the pixel values in the pre-processed video images are calculated to produce a sequence of logarithm images. The logarithm images are subject to a sunlight compensation in process 702 (to be explained below) and noise compensation and edge detection 703 (to be explained below), and the resultant images are combined to produce a movement image in step 704, which represents areas of the original image in which subject movement is likely to be present. This movement image is used for heart rate and breathing rate estimation in process 705 and for movement calculation in step 706.

In a parallel stream B, a noise image is calculated to indicate for the F' frames how much of the variation in pixel value at each of the x' by y' pixel positions is likely to be caused by pixel noise and how much by other sources. With a typical image sensor, as the image gets brighter, more pixel noise is expected and thus the amount of variability of the pixel value (e.g. the variance) is proportional to both the intensity and the shutter time. Because the analysis for subject movement, heart rate and breathing rate will depend on detecting the variation in pixel values, compensation for the pixel noise is advantageous. Thus in step 707 the video images are multiplied by their corresponding shutter times and further temporally resized by averaging all F' frames of the time window together. This results in a single frame of x' by y' pixel values. Then a kernel convolution is applied in step 708 to pre-adjust for the fact that an edge kernel convolution will be applied to the main image. Thus the noise kernel used in step 708 is the elementwise square of the edge kernel to be used in the main image analysis described below. The kernel depends on the target of the analysis: for heart rate estimation the edge kernel is the identity matrix (i.e. no convolution), for movement and breathing rate it is the Laplacian of Gaussian (LoG) kernel such as:

$$\begin{matrix} 0 & -1 & 0 \\ -1 & 4 & -1 \\ 0 & -1 & 0 \end{matrix}$$

Thus the noise kernel is the identity matrix for heart rate, but for movement detection and breathing rate estimation is:

$$\begin{matrix} 0 & 1 & 0 \\ 1 & 16 & 1 \\ 0 & 1 & 0 \end{matrix}$$

This convolution provides a noise image which will be used for noise compensation in calculation of the derivative image 703.

FIG. 8 is a flow diagram illustrating the generation of the movement image 704 through the application of global intensity variation compensation 702, spatial filtering 703 and noise compensation 709, to the sequence of log images 701.

To perform compensation for global intensity variations, such as sunlight, in step 800 the R background regions defined at set-up are taken and in step 801 the pixel values in the logarithm image in each of those R regions are averaged for each of the F' frames. This results in R signals each having F' sample values (the average intensity in that background region in that frame). Principal components analysis is then applied to the R signals in step 802 and in step 803 the standard deviation of each of the principal components is calculated. Only those principal components with a standard deviation above a threshold TH1 are retained. This results in r principal components which are expected to be representative of the main global intensity variations in the image, such as those caused by sunlight. These principal components will be used to de-correlate global intensity variations from the image under analysis.

Thus in a parallel stream 703, an edge image, in this case a derivative image is calculated which, for breathing rate and movement, represents the presence of edges (i.e. sharp changes in image intensity in the image frame). To obtain this edge image, in step 805 a convolution kernel, the Laplacian of Gaussian edge kernel, is applied to the logarithm image. In the case of movement detection and breathing rate estimation, which will be estimated based on subject movement in the image, the edge kernel may be:

$$\begin{matrix} 0 & -1 & 0 \\ -1 & 4 & -1 \\ 0 & -1 & 0 \end{matrix}$$

which is a spatial filter that detects edges in the image. It is equivalent to taking the second spatial derivative of the image intensity. Areas where the intensity is uniform are reduced to zero, and areas for which the intensity gradient is changing, as at an edge in the image, are enhanced.

An alternative method for creating the edge image would be to use a combination (usually the Euclidian norm) of horizontal and vertical Sobel (or Prewitt) filters applied to the image rather than calculating a derivative image using the above kernel. Another edge detection technique that can be used is the Canny edge detector, which builds upon the derivative to find linked edges and presents edges that are more likely to be true edges from the intensity image.

In the case of heart rate, the heart rate estimation will be estimated by looking for photoplethysmographic (PPG) signals in the image rather than movement. Consequently the edge kernel for heart rate estimation is the identity matrix.

Then in step 806 areas of the images that were predefined at set-up as unlikely to include subject movement are masked-out.

The resulting sequence of images is used in two ways. Firstly it is used in the elimination of global intensity variations, and secondly it is used to produce an image representing where subject movement is present. To compensate for global intensity variations, therefore, in step 806 the correlation is calculated between each of the r retained principal components of average intensity variations in the R predefined background regions and the sequence of images resulting from step 806. The result is a single frame correlation image of x' by y' pixels for each principal component, in which each pixel value is the correlation between the respective one of the r retained principal components and the variation through the F' frames at each x' by y' pixel position. The L2 norm is then applied framewise to produce a single correlation image representing the correlation across all the retained principal components.

The correlation image effectively indicates how much of the intensity variation in each pixel is likely to be a result of a global intensity variation.

Returning to the edge images, following masking-out of unwanted regions in step 806, in step 807 the amount of variability over the F' frames of each of the x' by y' pixels is quantified. One example of such quantification is to calculate the standard deviation over the F' frames. Other examples include the interquartile range in variation, the maximum range, etc. This results in step 808 in a standard deviation image consisting a single x' by y' image frame representing the amount of variation through the whole time window at each x',y' pixel position. In step 809 this is multiplied by the square root of the noise image calculated in step 709 to compensate for pixel noise. This effectively adjusts for the fact that, in a sequence of logged images containing no movement or illumination changes, the variability of dark pixels would inherently be higher than that of a bright pixel. Thus multiplying by the square root of the noise image effectively down-weights darker pixels.

In step 810 the noise-compensated standard deviation image is de-correlated against global intensity variations by multiplying by:

$$\sqrt{1-(\text{correlationimage})^p}$$

The power p is chosen between 0.5 and 2.0 and may be set experimentally by reference to video sequences from a particular set-up. A lower power tends to increase the degree of compensation for sunlight changes. The result is a single image of x' by y' pixel values which represent the amount of movement-related intensity variation in the video image over that time window. In step 811 a saturation mask is applied. The saturation mask eliminates areas where pixels have recorded an image intensity above a maximum or below a minimum brightness during the original F frames.

FIG. 9 illustrates an embodiment of constructing a saturation mask. In step 901 the original F x by y pixel video images are spatially resized by a factor of 0.5 in both vertical and horizontal directions in the image by averaging neighbouring pixels together. Then at each resized pixel position the pixel value is set to zero if the intensity value is greater than a pre-set maximum or less than a pre-set minimum at any point through the F frame time window. The F frames are then temporally resized over the whole time window by setting the pixel value to zero if that pixel is zero at any frame in the time window, or to one otherwise. This results in a single frame of x/2 by y/2 values that are zero or one. The mask is then dilated by at least one pixel by setting any pixel to zero if any of its eight nearest neighbours (Moore neighbourhood) are zero. This then forms a saturation mask which is applied in step 811 to the image from step 810 by multiplying the pixel values together. This eliminates from the image any areas where pixels were above the predetermined maximum intensity or below the predetermined minimum intensity in the time window.

Finally in step 812 a rescaling operation is applied by dividing each pixel value by (F'-1-r) where r is the number of retained principal components from step 806. This compensates for a possible variation in the number of retained principal components used in the global intensity variation compensation which would otherwise affect the result.

The result of step 812 is a single x' by y' frame of values which indicate how much intensity variation and edge movement exists in that pixel position in the time window. This can be regarded as a movement image for the time window and it will be used to quantify the amount of subject movement and for estimation of the subject's heart rate and breathing rate.

FIG. 10 illustrates one embodiment of how the movement image is used to provide status indications relating to movement of the subject. Recalling that the movement image is a single x' by y' frame of pixel values corresponding to the amount of variation of that pixel through the time window, in step 1001 for each of the predefined regions 9 where movement of the subject would be of interest (as set up in step 303), a movement value is selected as representative for the region and compared to a threshold. In this example the tenth largest pixel value is taken as the movement value, but a different pixel may be used, or some combination of pixel values, for instance the mean of the $92^{nd}$ to $97^{th}$ most intense pixel values. This movement value is then compared to a threshold and if it is above a predetermined threshold then movement is regarded as being present for that region and if it is below the threshold, movement is regarded as being not present for that region. It would be possible to take an ordinal other than the tenth largest value, for example values between the land 100 will work and the particular selection of the ordinal value taken is chosen by testing the algorithm on video images from a particular set up. Alternatively, the movement image can be spatially filtered before taking the nth highest value— Gaussian blur, morphological erosion, median blur, allowing the choice of a smaller value for n. Alternatively, a classifier, such as a convolutional neural network, may be trained and applied to classify movement images as either containing or not containing human movement.

Each time window of F frames thus provides a movement present or not present indication for each of the predetermined regions 9 in the room. As the process analyses the video image by looking at successive overlapping time windows, a next set of movement values for each predetermined region 9 in the room will be produced when the processing of the next time window has been completed. In this embodiment the time windows overlap by one second and thus a new movement indication is output for each region 9 every second.

In step 1003 the movement indications for the regions 9 optionally together with an indication of whether breathing has been detected, a door status signal 1004, and the estimates of heart rate and breathing rate are applied to an interpretation module for automatic interpretation of the subject status. The door status signal is based on a door sensor and indicates whether the door is open or closed and the time since closing or opening. Alternatively, the status of the door may be determined by conventional analysis of the video image and recognising the door as open or closed in the image. In this embodiment the door status signal has four states: 1) door open; 2) door unknown; 3) door recently shut (e.g. 0-29 seconds ago) and door prolongedly shut (eg. >29 seconds).

The interpretation module may be a logic engine using combinatorial logic to associate predefined subject statuses (e.g. alive, dead, sleeping, presence in different parts of the room, room unoccupied) with particular inputs of movement estimation, door status, and vital signs. The logic may be fixed, e.g. a tabulated relationship between the output statuses and the inputs, or the inputs may be applied to a state machine which has a plurality of predefined states corresponding to different conditions of the subject in the room and is operable to transition between those states in a predefined way based on the input of the subject movement and breathing rate. Alternatively a machine learning algorithm or expert system may be trained to output a classified subject statuses according to the inputs.

FIGS. 11 and 12 illustrate one embodiment of the processing to estimate the heart rate and breathing rate of the subject of step 705. The aim in this embodiment is to use the results of the movement detection above to narrow down the amount of image to be processed to derive accurate heart and breathing rate estimates. In step 1100 the x' by y' movement image from step 704 is taken and used to create a mask eliminating all but the top N-values where N is chosen according to the processing power available whilst remaining large enough to accurately produce the HR and BR estimates. For example, may be selected as the top 5000 pixels which is considerably less than the total number of pixels in the ' by y' frame. This therefore represents the locations in the image frame where subject movement is most likely. In step 1102 this movement mask is applied to each of the F' frames in the derivative image from step 805. Thus only those values are retained which are in areas of the image where movement is expected. image from step 805. Thus only those values are retained which are in areas of the image where movement is expected.

In step 1103 global intensity variations are removed by de-correlating the signals against the PCs from 804 as follows: From each signal a multiple of each PC is subtracted, where the multiples are chosen such that, after subtraction, the Pearson correlation between the signal and each PC is zero.

The variations in edge image values value at each of the x' by y' positions with time through the F' frames are taken as signals (x'×y' signals of length equal to the product of the frame rate and the time window duration). The signals are filtered according to the target of the analysis. For heart rate estimation a bandpass filter is applied to eliminate contributions which have a frequency outside the expected physiological range for heart rate. For example, a Butterworth bandpass filter may be used with a pass band of 0.7 to 2.5 Hz (44 to 150 beats per minute). To estimate breathing rate the signals are subject to linear de-trending and Gaussian smoothing.

The aim then is to reduce the number of signals by looking at indices of signal quality. As each time window will be generating N (5000 in the example above) signals, it is advantageous if signal quality indices which are quick to calculate are used in this first reduction of the number of signals for processing.

Thus, for example, peak consistency, amplitude consistency and wavelength consistency for each of the signals may be calculated to provide measures of periodicity. An indication of peak consistency is to take all the peak to peak or trough to trough times in each signal and calculate the standard deviation divided by the mean of those times. An indication of amplitude consistency is to take the standard deviation of the amplitude divided by the mean amplitude for the frequency window. An indication of wavelength consistency is to take the standard deviation of the times between mean crossings. In all three cases low values indicate greater consistency and thus that the signal is of higher quality.

In step 1105 these measures of consistency are multiplied together and a number of the best signals are taken, for example the top M. In this example M=200 but the exact number is not critical. Where more computing power is available for downstream processing, more signals may be taken.

In step 1106 principal components analysis is performed on these top M signals and a small number of the top principal components are retained. The number of retained principal components may vary with the target of the analysis. Typically between 3 and 10 may be chosen.

In step 1108 the frequencies of the retained principal components are calculated, these being candidate frequencies for the vital sign (heart rate or breathing rate) which is the target of the analysis. In step 1109 an estimate of the vital sign (heart rate or breathing rate) based on the frequency of the retained principal components is output. This estimate may be based on a confidence value calculated for each of the retained principal components in steps 1110 and 1112. This confidence value may be based on signal quality indices selected from: peak consistency, amplitude consistency, wavelength consistency, spatial dispersion (a measure of how the signals are spatially dispersed through the area of the image), the standard deviation of the signals, solidity (a measure of whether the signals are from clustered areas of the image), the uniformity of the signals and the amount of movement associated with the signal in the area the signal comes from (this is of interest because a high level of movement associated with a heart rate signal, for instance, indicates that the signal may be spurious). Other signal quality indices may be used in addition to or instead of these, or fewer of these may be used.

Examples of measures of the peak consistency and amplitude consistency were given above and the same measures may be used here.

A way of calculating a measurement of how each principal component is spatially dispersed through the image is to look at the loadings from each signal, i.e. how much of each of the 200 signals in step 1105 contribute towards it (this will be a 200 element column matrix). A distance matrix is constructed of, for example, the Euclidian distance in the image frames between all of the different possible pairs of the 200 signals in step 1105. This distance matrix (which will be a 200×200 element matrix) may be element-wise multiplied by the outer product of the absolute values of the principal component loadings (i.e. all pairs of the loadings multiplied together) to produce a 200×200 matrix of distances weighted by loading. Summing all of the values in this matrix gives a single value which is a measure of the spatial dispersion of the signals that contributed to the principal component. This spatial dispersion measure is, therefore, highest when the strongest contributing signals are far apart, and lower otherwise. It effectively measures the density of high loadings. This is a useful signal quality index because it would be expected that movement associated with a subject in the image would be strong and localised, rather than diffuse.

The spatial dispersion value is obtained for each principal component retained in step 1107.

The principal component loadings may also be used to calculate a signal quality index indicative of solidity. This is a measure of whether the signals that contribute to the retained principal components are from clustered areas of the image which would be expected for an area of skin of the subject. It is therefore a signal quality index which is effective at recognising a heart rate signal.

To calculate a solidity signal quality index for each retained principal component, absolute values of the loadings are taken together with the corresponding pixel locations for the two hundred signals of step 1105. The loadings are then placed into an x' by y' array (i.e. the same size as the image) in the corresponding x', y' location. This effectively creates a loadings image. A spatial filter is then applied to the loadings image, for example a median filter with a 3×3 kernel size, and this effectively favours areas which are clustered and have a high loading. Clustered areas where there are five non-zero values next to each other will retain a value, but areas which are isolated, i.e. surrounded by zeros, will themselves be set to zero. The solidity is then calculated as the sum of these retained values.

A different approach to calculating solidity would be to apply the density-based spatial clustering of applications with noise (DBSCAN) algorithm to the loadings image to determine the clustering of loadings. The solidity would be calculated from the sum of the loadings of values that belonged to clusters with a minimum size.

The size of the kernel in the spatial averaging filter may be varied depending on the resolution of the video camera and the expected size of skin areas in the image.

A signal quality index indicative of uniformity of the retained components may also be calculated from the principal component loadings. The absolute loadings may be subject to L1 normalisation (in which each value is divided by the total of the values) and then the result is cubed. The absolute values of the cubes are summed, and the total is then subtracted from 1, to give a single value indicative of the uniformity of the signal.

A different measure of uniformity can be generated by taking the inverse of the standard deviation of the loadings. This will be higher for components with less variability in their loadings.

A signal quality index which indicates the amount of movement associated with the signal in the area the signal comes from can be calculated by using the principal component loadings and in particular by thresholding the absolute values of the loadings to return a subset of the strongest loadings. This subset is used to determine which pixel locations in the movement image are associated with the signal by extracting the movement values from this set of pixel locations and taking a representative value, e.g. the median value, as the amount of movement SQI. The amount of movement is then judged as to whether it is appropriate or inappropriate for the signal detected—e.g. a heart rate signal should not be associated with a high level of movement. The method for finding this SQI can be varied within the same concept. For instance, it is alternatively possible to:

scale the movement values at each pixel by the associated loading value before finding the median;

find another representative value for the movement amount, e.g. the mean of the interquartile range of movement values instead of the median;

find the largest contiguous cluster of pixel locations in the movement image associated with the signal and take a representative (e.g. the mean) movement value from it;

use a movement image derived from dense optical flow, or in some other way, rather than the specific method detailed above;

and any valid combination of the above.

Having calculated a number of signal quality indices, these signal quality indices are then used to select amongst the principal component frequencies to output in step 1109 the best estimate of the vital sign (heart rate or breathing rate). One way of achieving this is to use the signal quality indices to calculate a single confidence value as indicated in step 1112. This can be done by logistic regression or by a machine learning technique trained on a data set for which the actual heart rate and breathing rate are known. For example, an artificial neural network may be trained to output a confidence value between zero and one based on the signal quality indices for each of the principal components from step 1107.

The confidence value and frequency of each principal component may then be input into a normal density filter, to output an estimate of the vital sign as shown in FIG. 12. For example, a histogram may be maintained with bins respectively corresponding to each possible output vital sign frequency and each of the frequencies from step 1108 may contribute to the appropriate histogram bin with a weight determined by its confidence value. The histogram will be updated once for each time window with the frequency values from step 1108 weighted by their confidence from step 1112. A proportion of each value weighted by the confidence may also be added to neighbouring bins in a normal distribution as indicated in step 1203. Preferably each of the existing histogram counts is decayed by a factor before being updated with the new values from the current time window as indicated by step 1206. A decay factor of 20%, for example, may be used for each process cycle (time window).

Whichever histogram bin has the highest count will be regarded as the current estimate of the vital sign, and the corresponding estimate is output and displayed in step 1205. The estimate is only output if the height of the bin exceeds a certain minimum threshold. If no bin exceeds the minimum threshold then no estimate of the vital sign is output.

The decay of existing values may be adjusted depending on the amount of movement detected in the image as indicated by step 1207. Consequently if the amount of subject movement is above a predetermined threshold, the decay may be increased, for example to 75%, to reduce the influence on the estimate of previous values. This also may result in the highest histogram count not exceeding the minimal threshold for output, which reflects the fact that when there is high subject movement in the image, estimates of heart rate and breathing rate will be less accurate and so the algorithm is less able to estimate the vital sign accurately.

As indicated above, the results of the video image analysis in the form of detected subject movement and any estimated vital signs may be output continuously on the display 9. In addition the system may provide summary reports relating to the movement pattern of the subject (based on detection of movement in the regions 9) and/or their vital signs, for example over a particular period. FIG. 13 illustrates an example report for the night time for a subject in a care home. In this example report on the left hand side is a colour-coded time bar for the period of night time in which periods in bed 140 and out of bed 141 are colour-coded differently, and the specific times for being out of bed and getting into bed are indicated too. Because of the ability of the process to detect movement at the door and whether or not the door is open, the activity report also includes a list 142 of room entry times. Summary indicators of the amount of time in bed 143, the number of times out of bed 144 and the number of room entries 145 may also be provided. The vital signs may be indicated at 146. This may be a simple indication of how many times vital signs were estimated, or an indication of the measured vital signs during the period can be given.

The invention may be embodied in a signal processing method, or in a signal processing apparatus which may be constructed as dedicated hardware or by means of a programmed general purpose computer or programmable digital signal processor. The invention also extends to a computer program for executing the method and to a storage medium carrying such a program.

The invention comprises the following embodiments and features two or more of which may be combined together.

A method of monitoring a human or animal subject comprising the steps of: capturing a video image of the subject consisting of a time series of image frames each frame comprising a pixel array of image intensity values; analysing the video image to determine automatically one or more regions of interest in the image in which variations in the image intensity contain signals representative of the physiological state of the subject, said signals comprising at least one vital sign and subject movement; analysing the intensity values in the regions of interest to determine subject movement and at least one vital sign of the subject; wherein the step of determining automatically one or more regions of interest in the image comprises analysing the image to measure the amount of variation in image intensity with time at each of a plurality of positions in the image, and selecting as regions of interest those positions at which the amount of variation in image intensity with time is above a predetermined threshold.

The method above may have one or more of the following optional features: Such a method wherein each of said plurality of positions comprises at least one pixel of the image. Such a method wherein each of said plurality of positions comprises a plurality of neighbouring, but not necessarily contiguous, pixels whose intensity values are combined together. Such a method wherein the number of neighbouring pixels whose intensity values are combined together is set to a first value for determining subject movement and to a second value, different from said first value, for determining said at least one vital sign. Such a method wherein the second value is set in dependence upon the vital sign being determined. Such a method wherein the video image is temporally resized before the analysing steps by combining together a plurality of successive frames of the video image. Such a method wherein the number of frames that are combined together is set to a first value if subject movement is being determined and to a second value, different from said first value, if a respiration rate of said subject is being determined. Such a method wherein predetermined areas of said video image are masked out before said analysing steps. Such a method wherein a function is applied to the image intensities that magnifies lower intensities and reduces the prominence of greater intensities to produce a non-linearly-scaled image, and the step of measuring the amount of variation in image intensity with time is conducted upon on the resultant image. Such a method wherein the logarithm of the image intensities is taken to form a logarithm image, and the step of measuring the amount of variation in image intensity with time is conducted upon on the logarithm image. Such a method wherein a function is applied to form an edge image which has high intensities at edges in the image, and the step of measuring the amount of variation in image intensity with time is conducted upon the edge image. Such a method wherein a kernel convolution is applied to form the edge image by calculating the derivative, and the step of measuring the amount of variation in image intensity with time is conducted upon on the derivative image. Such a method further comprising the step of detecting global intensity variations in the image and de-correlating the measured amount of variation in image intensity with time from the detected global intensity variations. Such a method wherein the step of detecting global intensity variations comprises detecting variations in image intensity in predefined areas of the image. Such a method wherein the step of detecting global intensity variations comprises detecting principal components in the variations in image intensity, and retaining as representative of global intensity variations only those principal components whose variability is above a predetermined threshold. Such a method further comprising the step of compensating the image for pixel noise by down-weighting signals having low image intensity.

Another embodiment, which may be used alone or with the embodiment above, provides a method of monitoring a human or animal subject comprising the steps of: capturing a video image of the subject consisting of a time series of image frames each frame comprising a pixel array of image intensity values; and analysing the video image to determine automatically one or more vital signs of the subject; wherein the step of determining automatically one or more vital signs of the subject comprises: analysing the image to detect a plurality of signals each comprising the variation in image intensity with time at each of a respective plurality of positions in the image, determining a first plurality of signal quality indices of the signals and retaining only those signals whose signal quality indices are above a predetermined threshold, analysing the retained signals in a multi-dimensional component analysis to obtain components thereof and retaining a predetermined number of the strongest components, determining a second plurality of signal quality indices of the retained components, selecting amongst the retained components on the basis of the second plurality of signal quality indices, determining the frequency of the selected components, and outputting a vital sign estimate based on said determined frequencies.

The methods above may have one or more of the following optional features: Such a method wherein each of said plurality of signals comprises the variation in intensity at a plurality of pixels in a local neighbourhood in each of said image frames whose intensity values are combined together to form one of said plurality of signals. Such a method wherein said positions are positions in the image at which subject movement has been detected. Such a method further comprising the step of frequency filtering each of said plurality of signals to exclude those outside predetermined expected physiological range for said one or more vital signs. Such a method further comprising the step of calculating the logarithm of said image intensity values to form a logarithm image and said step of analysing the image is performed on said logarithm image. Such a method wherein said first plurality of signal quality indices comprise measures of periodicity, for example one or more of peak consistency and amplitude consistency. Such a method wherein said step of multi-dimensional component analysis comprises decomposing the retained signals into their components, for example by one of principal component analysis or independent component analysis. Such a method wherein said second plurality of signal quality indices comprise measures of one or more of: periodicity, spatial distribution within the image, uniformity and variability of the component. Such a method further comprising the step of determining from said second plurality of signal quality indices a confidence value for each of said retained components and using said confidence value in said selecting step. Such a method wherein said selecting step comprises weighting said retained components by said confidence value and updating a prior estimate of said one or more vital signs by said weighted components. Such a method further comprising the step of down-weighting said prior estimate of said one or more vital signs by a predetermined amount before updating it with said weighted components. Such a method further comprising the step of detecting the amount of subject movement in the image and varying said predetermined amount in dependence upon the detected amount of subject movement. Such a method wherein the amount of subject movement is detected by determining the amount of variation in image intensity with time at each of said respective plurality of positions in the image. Such a method wherein said step of determining from said second plurality of signal quality indices a confidence value for each of said retained components is found using a machine learning technique.

Another embodiment, which may be used alone or with either or both of the embodiments above, provides a method of monitoring a human or animal subject comprising the steps of: capturing a video image of the subject consisting of a time series of image frames each frame comprising a pixel array of image intensity values; analysing the video image to detect signals comprising temporal variations in the image intensity representative of movement of the subject; and outputting an indication of the movement of the subject; wherein the step of analysing the video image to detect signals comprising temporal variations in the image intensity representative of movement of the subject comprises: measuring the variation with time of the image intensity at each of a plurality of positions in the image to form a respective plurality of movement signals; grouping the movement signals into a plurality of groups according to their position in the image, quantifying the variability in each of the movement signals and forming for each group a representative single movement signal, determining whether the variability of the representative movement signal is above a predetermined threshold, and determining movement as being present at that position in the image if the variability of the retained movement signal is above the predetermined threshold.

The methods above may have one or more of the following optional features: Such a method wherein the step of measuring the variation with time of the image intensity at each of a plurality of positions in the image comprises detecting spatial intensity variations representing edges in the image to form an edge image; and measuring the variation with time of the edge image at each of a plurality of positions in the image to form the respective plurality of movement signals. Such a method wherein the step of detecting spatial intensity variations representing edges in the image to form an edge image comprises applying a kernel convolution to each frame of the image, the kernel convolution combining the intensities of a plurality of neighbouring pixels in the frame to detect edges in the image. Such a method wherein a function is applied to the image intensities that magnifies lower intensities and reduces the prominence of greater intensities to produce a non-linearly-scaled image, and the step of measuring the amount of variation in image intensity with time is conducted upon on the resultant image. Such a method comprising the step of determining the logarithm of the image intensities in each frame to form a logarithm image and wherein said step of analysing is conducted upon the logarithm image. Such a method wherein the step of forming for each group a representative single movement signal comprises retaining for each group a predetermined ordinal one of the movement signals ordered by their variability, determining whether the variability of the retained movement signals are above a predetermined threshold, and determining movement as being present at that position in the image if the variability of the retained movement signal is above the predetermined threshold. Such a method wherein each of said plurality of positions comprises at least one pixel of the image. Such a method wherein the intensity values of a plurality of neighbouring pixels are combined together to form a spatially resized image upon which said analysis step is conducted. Such a method wherein a temporally resized image upon which said analysis step is conducted is formed by combining together corresponding pixel values in a plurality of successive frames of the video image. Such a method wherein predetermined areas of said video image are masked out. Such a method further comprising the step of detecting global intensity variations in the image and de-correlating them from the derivative image. Such a method wherein the step of detecting global intensity variations comprises detecting variations in image intensity in predefined areas of the image. Such a method wherein the step of detecting global intensity variations comprises detecting principal components in the variations in image intensity, and retaining as representative of global intensity variations only those principal components whose amplitude variability is above a predetermined threshold. Such a method further comprising the step of compensating the image for pixel noise by down-weighting signals having low image intensity.

The invention may be embodied as a system for monitoring a human or animal subject in accordance with the method above, comprising: a video camera adapted to capture a video image of the subject; a display; a video image processing unit adapted to process the image in accordance with the methods above.

The invention claimed is:

1. A method of monitoring a human or animal subject comprising the steps of:
    capturing a video image of the subject consisting of a time series of image frames each image frame comprising a pixel array of image intensity values; and
    analysing the video image to determine automatically a vital sign estimate of one or more vital signs of the subject; wherein the step of determining automatically the vital sign estimate of one or more vital signs of the subject comprises:
    analysing the video image to detect a plurality of signals each comprising the variation in the image intensity values with time at each of a respective plurality of positions in the video image,
    determining a first plurality of signal quality indices of the signals and retaining only those signals whose signal quality indices are above a predetermined threshold,
    analysing the retained signals in a multi-dimensional component analysis to obtain components thereof and retaining a predetermined number of the strongest components,
    determining a second plurality of signal quality indices of the retained components,
    selecting amongst the retained components on the basis of the second plurality of signal quality indices,
    determining a confidence value and the frequency of each of the selected components, and
    outputting the vital sign estimate based on said determined frequencies, wherein the determined frequency of each selected component contributes to the vital sign estimate with a weight determined by the confidence value of the selected component.

2. A method according to claim 1 wherein each of said plurality of signals comprises the variation in intensity at a plurality of pixels in a local neighbourhood in each of said image frames whose image intensity values are combined together to form one of said plurality of signals.

3. A method according to claim 1 wherein said positions are positions in the video image at which subject movement has been detected.

4. A method according to claim 1 further comprising the step of frequency filtering each of said plurality of signals to exclude those outside predetermined expected physiological range for said one or more vital signs.

5. A method according to claim 1 further comprising the step of calculating the logarithm of said image intensity values to form a logarithm image and said step of analysing the video image is performed on said logarithm image.

6. A method according to claim 1 wherein said first plurality of signal quality indices comprise measures of periodicity, for example one or more of peak consistency and amplitude consistency.

7. A method according to claim 1 wherein said step of multi-dimensional component analysis comprises decomposing the retained signals into their components, for example by one of principal component analysis or independent component analysis.

8. A method according to claim 1 wherein said second plurality of signal quality indices comprise measures of one or more of: periodicity, spatial distribution within the video image, uniformity and variability of the component, amount of movement associated with the component.

9. A method according to claim 1 further comprising the step of determining from said second plurality of signal quality indices a confidence value for each of said retained components and using said confidence value in said selecting step.

10. A method according to claim 9 wherein said selecting step comprises weighting said retained components by said confidence value and updating a prior estimate of said one or more vital signs by said weighted components.

11. A method according to claim 10 further comprising the step of down-weighting said prior estimate of said one or more vital signs by a predetermined amount before updating it with said weighted components.

12. A method according to claim 11 further comprising the step of detecting the amount of subject movement in the video image and varying said predetermined amount in dependence upon the detected amount of subject movement.

13. A method according to claim 11 wherein the amount of subject movement is detected by determining the amount of variation in image intensity with time at each of said respective plurality of positions in the video image.

14. A method according to claim 9 wherein said step of determining from said second plurality of signal quality indices a confidence value for each of said retained components is found using a machine learning technique.

15. A system for monitoring a human or animal subject in accordance with the method of claim 1, comprising:
    a video camera adapted to capture a video image of the subject;
    a display;
    a video image processing unit adapted to process the video image in accordance with the method of claim 1.

16. A method of monitoring a human or animal subject comprising
    capturing a video image of the subject consisting of a time series of image frames each image frame comprising a pixel array of image intensity values; and
    analysing the video image to determine automatically one or more vital signs of the subject; wherein the determining automatically one or more vital signs of the subject comprises:
    analysing the image to detect a plurality of signals each comprising the variation in image intensity with time at each of a respective plurality of positions in the image,
    determining a first plurality of signal quality indices of the signals and retaining only those signals whose signal quality indices are above a predetermined threshold,
    analysing the retained signals in a multi-dimensional component analysis to obtain components thereof and retaining a predetermined number of the strongest components,
    determining a second plurality of signal quality indices of the retained components,
    selecting amongst the retained components on the basis of the second plurality of signal quality indices, determining the frequency of the selected components, and outputting a vital sign estimate based on said determined frequencies; and determining from said second plurality of signal quality indices a confidence value for each of said retained components and using said confidence value in said selecting, wherein said selecting comprises weighting said retained components by said confidence value and updating a prior estimate of said one or more vital signs by said weighted components.

17. A method according to claim 16 wherein said selecting step comprises weighting said retained components by said confidence value and updating a prior estimate of said one or more vital signs by said weighted components.

18. A method according to claim 17 further comprising the step of down-weighting said prior estimate of said one or more vital signs by a predetermined amount before updating it with said weighted components.

19. A method according to claim 18 wherein at least one of:

the method further includes the step of detecting the amount of subject movement in the video image and varying said predetermined amount in dependence upon the detected amount of subject movement; and the amount of subject movement is detected by determining the amount of variation in image intensity with time at each of said respective plurality of positions in the video image.

20. A method according to claim 16 wherein said step of determining from said second plurality of signal quality indices a confidence value for each of said retained components is found using a machine learning technique.

* * * * *